United States Patent
Giangrande et al.

(10) Patent No.: US 10,633,410 B2
(45) Date of Patent: Apr. 28, 2020

(54) NUCLEIC ACID APTAMERS TO TREAT HISTONE-INDUCED DISEASE STATES

(71) Applicants: UNIVERSITY OF IOWA RESEARCH FOUNDATION, Iowa City, IA (US); Paloma H. Giangrande, Iowa City, IA (US); Kevin Urak, Iowa City, IA (US)

(72) Inventors: Paloma H. Giangrande, Iowa City, IA (US); Francis Miller, Iowa City, IA (US); Kevin Urak, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/538,106

(22) PCT Filed: Dec. 22, 2015

(86) PCT No.: PCT/US2015/067516
§ 371 (c)(1),
(2) Date: Jun. 20, 2017

(87) PCT Pub. No.: WO2016/106387
PCT Pub. Date: Jun. 30, 2016

(65) Prior Publication Data
US 2018/0134746 A1   May 17, 2018

Related U.S. Application Data

(60) Provisional application No. 62/095,530, filed on Dec. 22, 2014.

(51) Int. Cl.
| | | |
|---|---|---|
| C12N 15/115 | (2010.01) | |
| C07H 21/02 | (2006.01) | |
| A61P 29/02 | (2006.01) | |
| A61K 9/00 | (2006.01) | |

(52) U.S. Cl.
CPC ............. *C07H 21/02* (2013.01); *A61K 9/007* (2013.01); *A61K 9/0019* (2013.01); *A61P 29/02* (2018.01); *C12N 15/115* (2013.01); *C12N 2310/16* (2013.01); *C12N 2310/321* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 8,716,218 B2 | 5/2014 | Esmon et al. | |
| 2009/0117099 A1 | 5/2009 | Esmon et al. | |
| 2014/0056959 A1 | 2/2014 | Giangrande et al. | |
| 2014/0234209 A1 | 8/2014 | Chang et al. | |

FOREIGN PATENT DOCUMENTS

WO   2010019446 A1   2/2010

OTHER PUBLICATIONS

Williams et al., Evolution of a histone H4-K16 acetyl-specific DNA aptamer, 2009, JACS, vol. 131, pp. 6330-6331.*
Abrams, et al., "Circulating Histones Are Mediators of Trauma-associated Lung Injury", American Journal of Respiratory and Critical Care Medicine 187, 160-169 (2013).
Allam, et al., "Extracellular histones in tissue injury and inflammation", Journal of Molecular Medicine 92, 465-472 (2014).
Behlke, "Chemical modification of siRNAs for in vivo use", Oligonucleotides 18, 305-319 (2008).
Bosmann, "Extracellular histones are essential effectors of C5aR- and C5L2-mediated tissue damage and inflammation in acute lung injury", The FASEB Journal 27, 5010-5021 (2013).
Chen, et al., "Release and activity of histone in diseases", Cell Death Dis 5, e1370 (2014).
Dassie, et al., "Targeted inhibition of prostate cancer metastases with an RNA aptamer to prostate-specific membrane antigen", Molecular Therapy 22(11), 1910-1922 (2014).
Grailer, et al., "Lung inflammation and damage induced by extracellular histones", Inflammation and Cell Signaling 1(4), doi:10.14800/ics.131, 5 pages (2014).
Hernandez, et al., "Methods for Evaluating Cell-Specific, Cell-Internalizing RNA Aptamers", Pharmaceuticals 6, 295-319 (2013).
Huang, et al., "RNA Aptamer-Based Functional Ligands of the Neurotrophin Receptor, TrkB", Mol Pharmacol 82, 623-635 (2012).
Hyun, et al., "An RNA aptamer that selectively recognizes symmetric dimethylation of arginine 8 in the histone H3 N-terminal peptide", Nucleic Acid Therapeutics 12(17), 2659-2666 (2011).

(Continued)

*Primary Examiner* — Dana H Shin
(74) *Attorney, Agent, or Firm* — Viksnins Harris Padys Malen LLP

(57) ABSTRACT

The present invention relates to methods of using optimized aptamers. In certain embodiments, the present invention provides a method for treating a subject having or being disposed to having a histone-induced injury or disease comprising administering to the subject a pharmaceutical composition comprising a pharmaceutically acceptable carrier and (i) a nucleic acid molecule not more than 90 nucleotides in length comprising an aptamer KU1, KU2, KU3, KU4, KU5, KU6, KU&, KU8, or KU9, wherein the aptamer specifically targets extracellular histones, wherein the nucleotides are RNA; or (ii) a conjugate comprising a nucleic acid molecule not more than 90 nucleotides in length comprising an aptamer KU1, KU2, KU3, KU4, KU5, KU6, KU&, KU8, or KU9, wherein the aptamer specifically targets extracellular histones, wherein the nucleotides are RNA, wherein the nucleic acid molecule is linked to a therapeutic molecule.

17 Claims, 25 Drawing Sheets
Specification includes a Sequence Listing.

(56) References Cited

OTHER PUBLICATIONS

Judge, et al., "Design of noninflammatory synthetic siRNA mediating potent gene silencing in vivo", Mol Ther 13, 494-505 (2006).
Kaul, et al., "Performance of the BioPlex™ 2200 Autoimmune Vasculitis kit", Autoimmun Rev 8, 224-227 (2009).
Keefe, et al., "Aptamers as therapeutics", Nat Rev Drug Discov 9, 537-550 (2010).
Patent Cooperation Treaty, International Searching Authority, Search Report and Written Opinion for PCT/US2015/67516, 13 pages, dated Jul. 12, 2016.
Semeraro, et al., "Extracellular histones promote thrombin generation through platelet-dependent mechanisms: involvement of platelet TLR2 and TLR4", Blood 118, 1952-1961 (2011).
Thiel, et al., "Delivery of chemo-sensitizing siRNAs to HER2+- breast cancer cells using RNA aptamers", Nucl Acids Res. vol. 40 (13), 6319-6337 (2012).
Thiel, et al., "Nucleotide bias observed with a short SELEX RNA aptamer library", Nucleic Acid Ther 21, 253-263 (2011).
Thiel, et al., "Rapid Identification of Cell-Specific, Internalizing RNA Aptamers with Bioinformatics Analyses of a Cell-Based Aptamer Selction", PLOS One, 7(9), e43836 (2012).
Thomas, et al., "Extracellular DNA traps are associated with the pathogenesis of TRALI in humans and mice", Blood 119, 6335-6343 (2012).
Tuerk, et al., "Systematic evolution of ligands by exponential enrichment: RNA ligands to bacteriophage T4 DNA polymerase", Science 249, 505-510 (1990).
Wong, et al., "A double-filter method for nitrocellulose-filter binding: application to protein-nucleic acid interactions", Proc Natl Acad Sci 90, 5428-5432 (1993).
Xu, et al., "Altmetric: 7Citations: 530More detail Letter Extracellular histones are major mediators of death in sepsis", Nature Medicine 15, 1318-1321 (2009).
Yu, et al., "Aptamers can discriminate alkaline proteins with high specificity", Chembiochem 12(17), 2659-2666 (2011).
Urak, et al., "Neutralization of extracellular histones with nucleic acid aptamers for the treatment of critical illness", Oligonucleotide Therapeutics Society, Annual Meeting, Montreal, Canada, 2 pages, Sep. 25-28, 2016.
Urak, et al., "RNA inhibitors of nuclear proteins implicated in multiple organ dysfunction syndrome", American Society of Gene and Cell Therapy, Chicago, Illinois, 2 pages (2018).
Urak, et al., "Treatment of sepsis by neutralization of extracellular histones with nucleic acid aptamers", Molecular Therapy 25(5), Cambridge, MA 02139 USA: Cell Press, 1 page (2017).

* cited by examiner

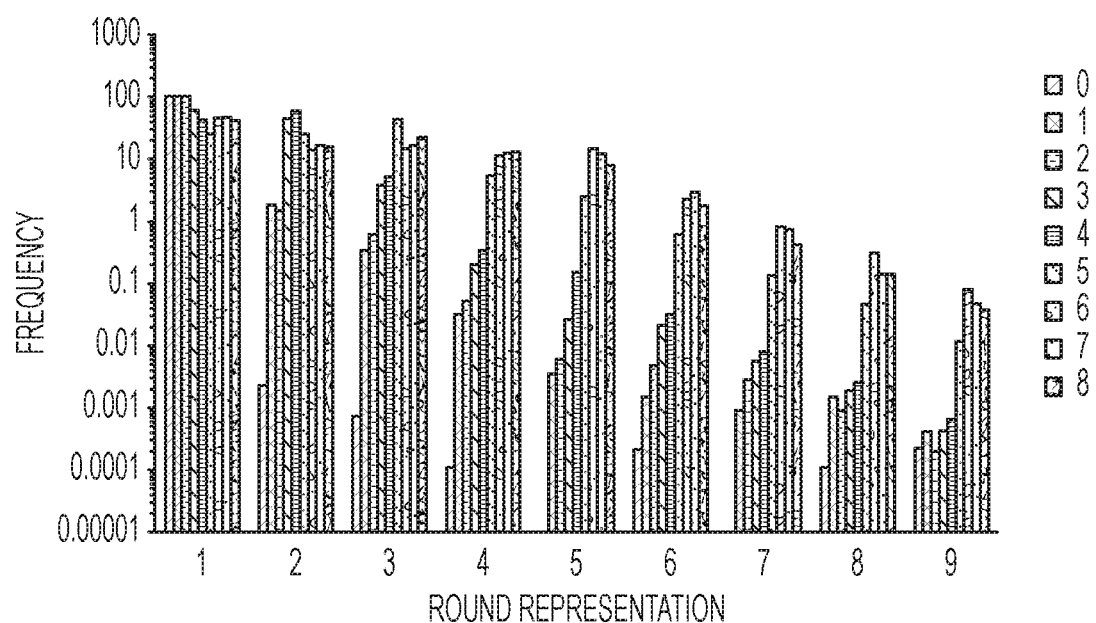
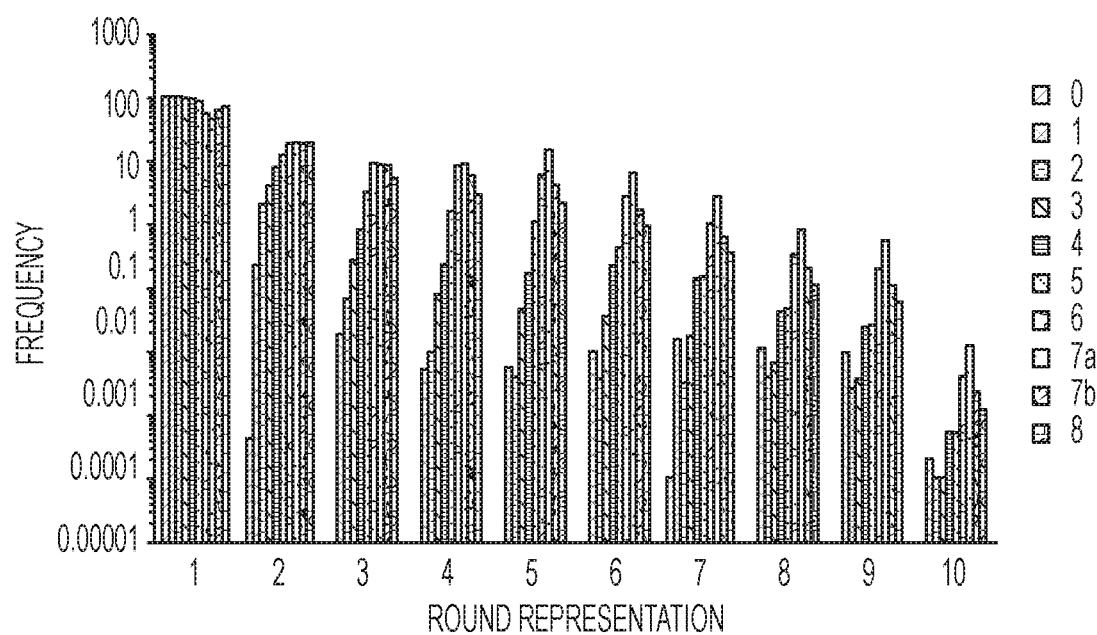
FIG. 9B

| ORIGINAL NAME | SEQUENCE | NAME |
|---|---|---|
| 0002_h3.2/0004_H4 | GGGAGGACGAUGCGGUUGGGUGUAGGGUGUACCGCAGACGACUCGCCCGA | KU1 |
| 0023_H32/0008_H4 | GGGAGGACGAUGCGGUUGAAGGUGAUGGUCCCAGACGACUCGCCCGA | KU2 |
| 0024_H32/0021_H4 | GGGAGGACGAUGCGGUUGAAGGUGAUGGUCCGCAGACGAUCGCCCGA | KU3 |
| 0081_H4 | GGGAGGACGAUGCGGAUCUUUUCUUUCUGCCGCAGACGACUCGCCCGA | KU4 |
| 0065_H4 | GGGAGGACGAUGCGGUUUAUUUCUUUCCACGUUCCGCAGACGACUCGCCCGA | KU5 |
| 0120_H4 | GGGAGGACGAUGCGGUUGUAAUUCUUGUUCCGCAGACGACUCGCCCGA | KU6 |
| 0145_H32 | GGGAGGACGAUGCGGAUGGAGGAGGUCCGCAGACGACUCGCCCGA | KU7 |
| 0236_H32 | GGGAGGACGAUGCGGAUGGAGGAGUGGGAGGUCCGCAGACGACUCGCCCGA | KU8 |
| 0243_H32 | GGGAGGACGAUGCGGAUUGGUGAAGUGAGGUACUGCAGACGACUCGCCCGA | KU9 |

FIG. 10

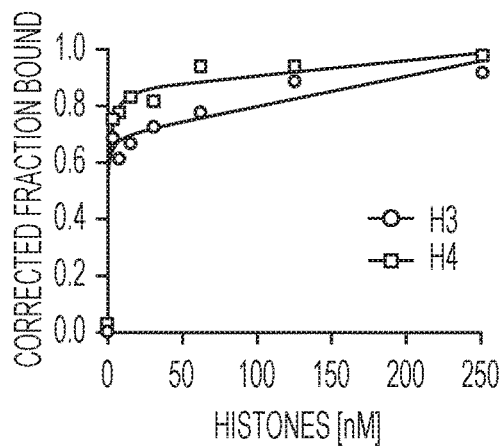
FIG. 16G
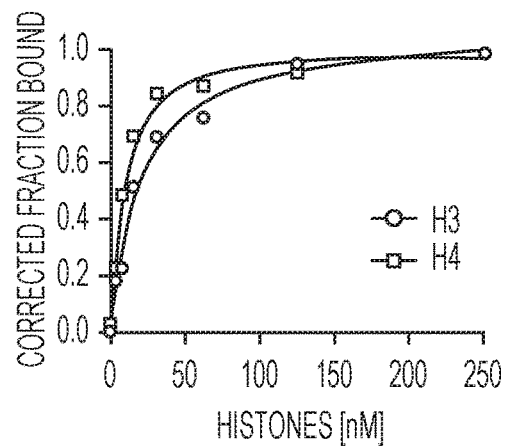
FIG. 16H
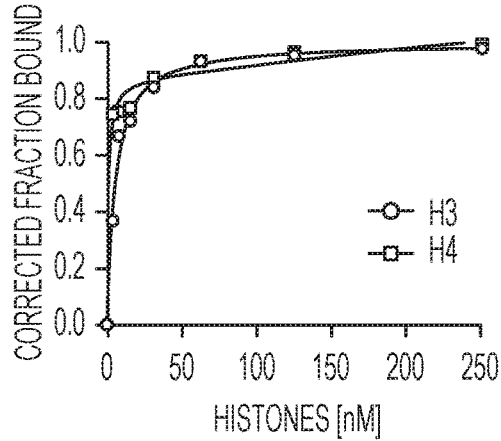
FIG. 16I
| CLONE BINDING AFFINITY TO HISTONE H3 AND H4 | | | | | |
|---|---|---|---|---|---|
| KU1 | $K_D$ (nM) | KU4 | $K_D$ (nM) | KU7 | $K_D$ (nM) |
| H4 | 2.156 | H4 | 18.77 | H4 | 0.41 |
| H3 | 30.18 | H3 | 23.50 | H3 | 2.5 |
| KU2 | $K_D$ (nM) | KU5 | $K_D$ (nM) | KU8 | $K_D$ (nM) |
| H4 | 14.28 | H4 | 0.21 | H4 | 9.463 |
| H3 | 18.40 | H3 | 0.79 | H3 | 19.45 |
| KU3 | $K_D$ (nM) | KU6 | $K_D$ (nM) | KU9 | $K_D$ (nM) |
| H4 | 15.33 | H4 | 0.8234 | H4 | 7.641 |
| H3 | 87.43 | H3 | 1.396 | H3 | 11.17 |
FIG. 17

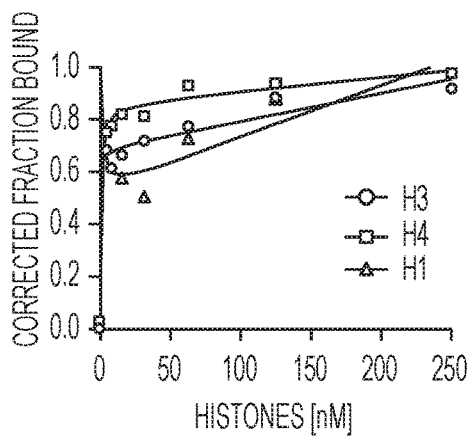
FIG. 18G
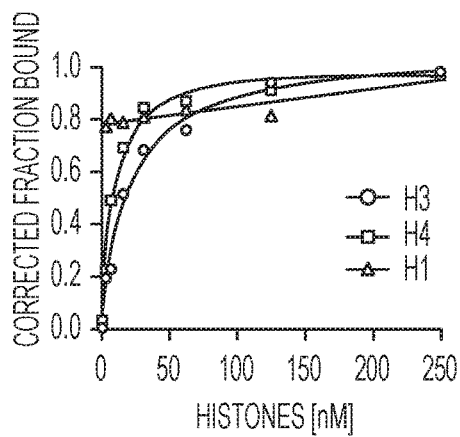
FIG. 18H
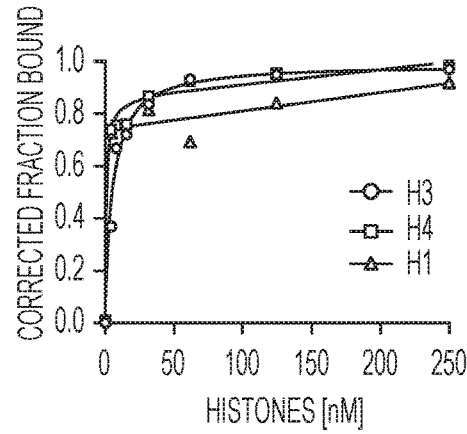
FIG. 18I
| CLONE BINDING AFFINITY TO HISTONE H1, H3, AND H4 | | | | | |
|---|---|---|---|---|---|
| KU1 | K$_D$ (nM) | KU4 | K$_D$ (nM) | KU7 | K$_D$ (nM) |
| H1 | NA | H1 | 2.951 | H1 | NA |
| H4 | 2.156 | H4 | 18.77 | H4 | 0.41 |
| H3 | 30.18 | H3 | 23.50 | H3 | 2.5 |
| KU2 | K$_D$ (nM) | KU5 | K$_D$ (nM) | KU8 | K$_D$ (nM) |
| H1 | NA | H1 | NA | H1 | .035 |
| H4 | 14.28 | H4 | 0.21 | H4 | 9.463 |
| H3 | 18.40 | H3 | 0.79 | H3 | 19.45 |
| KU3 | K$_D$ (nM) | KU6 | K$_D$ (nM) | KU9 | K$_D$ (nM) |
| H1 | 10220 | H1 | .6051 | H1 | NA |
| H4 | 15.33 | H4 | .38 | H4 | 7.641 |
| H3 | 87.43 | H3 | 1.396 | H3 | 11.17 |
FIG. 19

| CLONE BINDING AFFINITY TO HISTONE H3, H4, AND HUMAN SERUM ||||||||
|---|---|---|---|---|---|---|---|
| KU1 | $K_D$ (nM) | | KU4 | $K_D$ (nM) | | KU7 | $K_D$ (nM) |
| HUMAN SERUM | NA | | HUMAN SERUM | NA | | HUMAN SERUM | NA |
| H4 | 2.156 | | H4 | 18.77 | | H4 | 0.41 |
| H3 | 30.18 | | H3 | 23.50 | | H3 | 2.5 |
| KU2 | $K_D$ (nM) | | KU5 | $K_D$ (nM) | | KU8 | $K_D$ (nM) |
| HUMAN SERUM | NA | | HUMAN SERUM | NA | | HUMAN SERUM | NA |
| H4 | 14.28 | | H4 | 0.21 | | H4 | 9.463 |
| H3 | 18.40 | | H3 | 0.79 | | H3 | 19.45 |
| KU3 | $K_D$ (nM) | | KU6 | $K_D$ (nM) | | KU9 | $K_D$ (nM) |
| HUMAN SERUM | NA | | HUMAN SERUM | NA | | HUMAN SERUM | NA |
| H4 | 15.33 | | H4 | .38 | | H4 | 7.641 |
| H3 | 87.43 | | H3 | 1.396 | | H3 | 11.17 |
FIG. 21
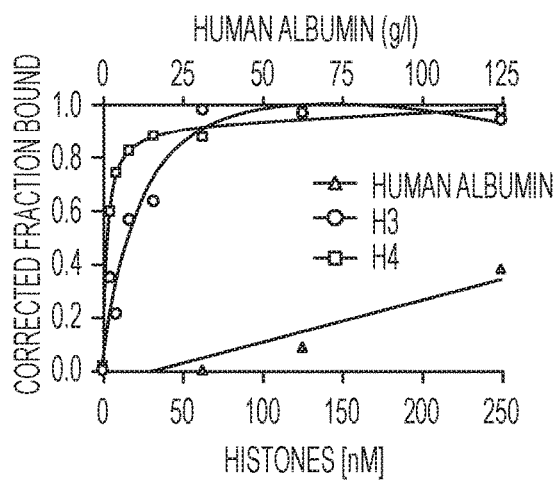
FIG. 22A
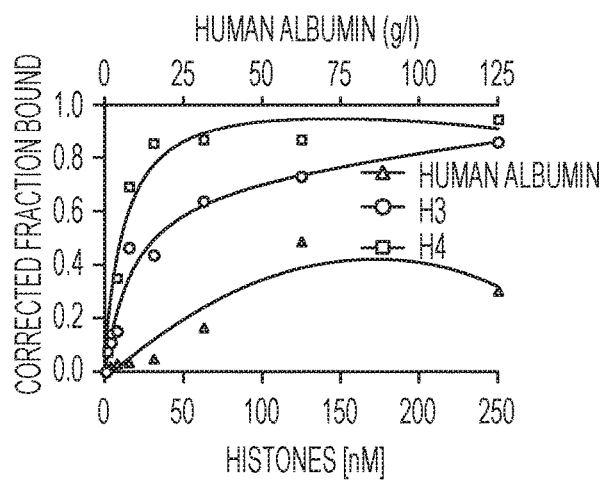
FIG. 22B

| CLONE BINDING AFFINITY TO HISTONE H3, H4, AND HUMAN ALBUMIN | | | | | | | | |
|---|---|---|---|---|---|---|---|---|
| KU1 | $K_D$ (nM) | | KU4 | $K_D$ (nM) | | KU7 | $K_D$ (nM) | |
| HUMAN ALBUMIN | NA | | HUMAN ALBUMIN | NA | | HUMAN ALBUMIN | NA | |
| H4 | 2.156 | | H4 | 18.77 | | H4 | 0.41 | |
| H3 | 30.18 | | H3 | 23.50 | | H3 | 2.5 | |
| KU2 | $K_D$ (nM) | | KU5 | $K_D$ (nM) | | KU8 | $K_D$ (nM) | |
| HUMAN ALBUMIN | NA | | HUMAN ALBUMIN | NA | | HUMAN ALBUMIN | NA | |
| H4 | 14.28 | | H4 | 0.21 | | H4 | 9.463 | |
| H3 | 18.40 | | H3 | 0.79 | | H3 | 19.45 | |
| KU3 | $K_D$ (nM) | | KU6 | $K_D$ (nM) | | KU9 | $K_D$ (nM) | |
| HUMAN ALBUMIN | NA | | HUMAN ALBUMIN | NA | | HUMAN ALBUMIN | NA | |
| H4 | 15.33 | | H4 | .38 | | H4 | 7.641 | |
| H3 | 87.43 | | H3 | 1.396 | | H3 | 11.17 | |

| CLONE BINDING AFFINITY TO HISTONE H1,H2,H2A,H2B,H3, AND H4 | | | | | | | |
|---|---|---|---|---|---|---|---|
| KU5 | K$_D$ (nM) | | KU7 | K$_D$ (nM) | | KU9 | K$_D$ (nM) |
| H4 | 0.2 | | H4 | 0.4 | | H4 | 7.6 |
| H3 | 0.8 | | H3 | 2.5 | | H3 | 11.2 |
| H2B | 2.5 | | H2B | 8.4 | | H2B | NA |
| H2A | 7.5 | | H2A | NA | | H2A | NA |
| H1 | NA | | H1 | 5.0 | | H1 | 5.3 |

NUCLEIC ACID APTAMERS TO TREAT HISTONE-INDUCED DISEASE STATES

RELATED APPLICATIONS

This application is a U.S. national phase application under 35 U.S.C. § 371 of PCT/US2015/067516, filed Dec. 22, 2015, which claims the benefit of priority of U.S. Provisional Application Ser. No. 62/095,530 filed on Dec. 22, 2014, which application is herein incorporated by reference.

SEQUENCE LASTING

The instant application contains a Sequence Listing which has been submitted electronically in ASCII format and is hereby incorporated by reference in its entirety. Said ASCII copy, created on Feb. 2, 2016, is named 17023.163WO1_SL.txt and is 3,639,382 bytes in size.

BACKGROUND OF THE INVENTION

A challenging medical problem often observed in critically ill patients is that in response to severe injury or illness, even those organs not directly affected by the original problem become dysfunctional. For example, patients with severe infection will often develop respiratory failure requiring mechanical ventilation, renal failure requiring dialysis, hepatic dysfunction, coagulation abnormalities, and hypotension requiring vasopressors. This condition, known as the multiple organ dysfunction syndrome (MODS), or by, some of its more prominent manifestations such as acute respiratory distress syndrome (ARDS), can be reversible, but the only treatment is supportive care as there is no therapy to directly prevent or reverse MODS. The incidence of MODS in intensive care unit (ICU) patients is 10-40% and the incidence of death in MODS is 40-50%. Even with survival, organ recovery can take months with significant associated morbidity and cost.

The annual incidence of acute lung injury (ALI) and acute respiratory distress syndrome (ARDS) approximates 200,000 cases in the United States, with mortality approaching 40%. Despite extensive research into the pathogenesis of ALI and clinical trials testing new therapeutics, the improvement in outcomes following ARDS over the past decade are due to improved strategies of mechanical ventilation and advanced support of other failing organs, as there remains no effective pharmacotherapy to treat patients with this syndrome. Furthermore, patients who survive frequently have significant psychological and physical morbidity, residual physical limitations and poor quality of life. The development of ALI/ARDS occurs as a consequence of critical illness of diverse etiologies; however, many of these are highly relevant to the military. For example, despite surviving an initial major trauma (e.g., blast and/or explosive), there is a high mortality associated with the subsequent development of multiple organ dysfunction syndrome (MODS). Postmortem findings show the lungs to be more frequently affected than any other organ in patients who die after trauma. In addition to trauma, other combat and military related causes of ALI/ARDS include toxic inhalation, burns, near-drowning, radiation, sepsis, and blood transfusion. The underlying pathological changes include neutrophil infiltration, pulmonary edema, hemorrhage, and microvascular thrombosis. There are no current methods to prevent the onset of MODS, only treatment of its effects. Thus, there is an on-going need for effective treatments to prevent the development of these syndromes.

SUMMARY OF THE INVENTION

The present invention is transformative because it develops an innovative treatment with preventing the development of MODS/ARDS in high risk patients. Extracellular histones are targeted with RNA aptamers in order to terminate the self-propagating cycle of tissue injury responsible for MODS/ARDS. By interrupting the cycle of histone-mediated cell injury, these histone-specific aptamers save lives and reduce the morbidity and the financial cost of multiple severe illnesses in thousands of patients.

Certain embodiments of the present invention provide a nucleic acid molecule not more than 100 nucleotides in length (e.g., 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt) comprising an aptamer, wherein the aptamer specifically targets histones. In certain embodiments, the aptamer specifically targets both H3 and/or H4. In certain embodiments, the aptamer specifically targets both human H3 and H4.

In certain embodiments, the nucleotides are RNA. In certain embodiments, the nucleic acid of the present invention is DNA. In certain embodiments, the RNA includes a modified nucleotide.

In certain embodiments, the nucleic acid molecule comprises a chemically modified. RNA comprising a 2' substituted sugar such as 2'-O-methyl-; 2'-O-(2-methoxyethyl); 2-O-alkyl; 2-O-allyl; 2'-S-alkyl; 2'-S-allyl; 2'-fluoro-; 2'-amino; 2'-halo or 2-azido-ribose, a carbocyclic sugar analogue, an a-anomeric sugar; an epimeric sugar such as arabinose, xylose or lyxose, a pyranose sugar, a furanose sugar, sedoheptulose; 2'-fluoro-β-D-arabinonucleotide (FANA) modification; a Locked nucleic acid (LNA).

In certain embodiments, the 2'OMe modified bases are alternated with un-modified RNA bases.

In certain embodiments, the chemically modified RNA comprises a 2'-fluoro pyrimidine and/or a 2' O-methyl pyrimidine.

In certain embodiments, the nucleic acid molecule comprises an 2'OMe purine and a 2'-fluoro pyrimidine.

In certain embodiments, the nucleic acid comprises a bridging, phosphorothioate, and end cap that reverses the polarity of the chain and/or a linker.

Certain embodiments of the present invention provide a conjugate comprising the nucleic acid molecule described above linked to a therapeutic or diagnostic molecule.

Certain embodiments of the present invention provide a pharmaceutical composition comprising a molecule or conjugate as described above and a pharmaceutically acceptable carrier.

Certain embodiments of the present invention provide a method for delivering a therapeutic or diagnostic molecule to a subject having or being disposed to having MODS/ARDS, comprising contacting the subject with the conjugate described above. In certain embodiments, the administration is by intravenous injection or by inhalation. In certain embodiments, the composition is administered within 0-24 hours after an injury. In certain embodiments, the composition is administered within 0-12 hours after an injury. In certain embodiments, the injury is trauma, burn, sepsis, transfusion-related acute lung injury, organ ischemia or diagnosis of illness, or inhalation lung injury. In certain embodiments, the composition is administered in response to a prolonged severe illness. In certain embodiments, the composition is administered multiple times, such as two, three, four, five or six times.

Certain embodiments of the present invention provide a use of a molecule or conjugate as described above for treating MODS/ARDS.

Certain embodiments of the present invention provide a molecule or conjugate as described above for use in therapy.

Certain embodiments of the present invention provide a molecule or conjugate as described above for use in the prophylactic or therapeutic treatment of a histone-induced disease. In certain embodiments, the disease is autoimmune disease (such as systemic lupus erythematosus), arthritis, rheumatoid arthritis, juvenile arthritis; edema; sepsis; septic shock; inflammation; non-septic hyper inflammatory disorder; infectious disease; thrombosis; nephritis; inflammatory liver injury; traumatic hemorrhage; acute pancreatitis; acute respiratory distress syndrome; ischemic injury; ischemic-reperfusion injury; ischemic stroke; cardiovascular disease; atherosclerosis; myocardial infarction; radiotherapy toxicity; cytokine therapy toxicity; granulomatous disease; asthma; graft-vs. host disease, cachexia, a coagulopathy; inhalation injury, trauma, cancer; or burn effects, multiple organ dysfunction syndrome (MODS)/acute respiratory distress syndrome (ARDS), and complications thereof.

In certain embodiments, the method further comprising administering at least one other therapeutic agent to the subject, before, concurrently with or after the composition. The present invention further provides a nucleic acid coding molecule encoding a nucleic acid aptamer molecule as described above.

In certain embodiments, the therapeutic agent is selected from the group consisting of an antibody, an antibody fragment, an immune conjugate, a radionuclide, an immunomodulatory, an anti-angiogenic agent, a pro-apoptotic agent, a cytokine, chemokine a drug, a toxin, a hormone, an siRNA, a cytokine, a chemokine, a coagulation inhibitor, a stem cell growth factor, a lymphotoxin, a hematopoietic factor, a colony stimulating factor, an interferon, erythropoietin, thrombopoietin, an enzyme, recombinant human thrombomodulin and activated human protein C.

As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the aptamer. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the RNA aptamers are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional sequences, such as sequences encoding an aptamer.

In one embodiment, pharmaceutical compositions will comprise sufficient genetic material to produce a therapeutically effective amount of the aptamer of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydro bromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available REMINGTON'S PHARMACEUTICAL SCIENCES (Mack Pub. Co., N.J. 1991).

BRIEF DESCRIPTION OF DRAWINGS

FIGS. 9A-9B. Bioinformatics analysis of selected rounds.

FIG. 10. Selected aptamer sequences #1 (SEQ ID NOS 7598, 7619, 7620, 10754, 10749, 10765, 7741, 7832, and 7839, respectively, in order of appearance).

FIGS. 16A-16I. Binding of individual RNA aptamers to histones H3 and H4.

FIG. 17. Table of binding affinities.

FIGS. 18A-18I. Binding data of individual RNA aptamers to histones H1, H3 and H4.

FIG. 19. Table of binding affinities.

FIG. 21. Table of binding affinities.

FIGS. 22A-22I. Binding data of individual RNA aptamers to histones H3 and H4, and human albumin.

FIG. 23. Table of binding affinities.

DETAILED DESCRIPTION OF THE INVENTION

Figure 1:
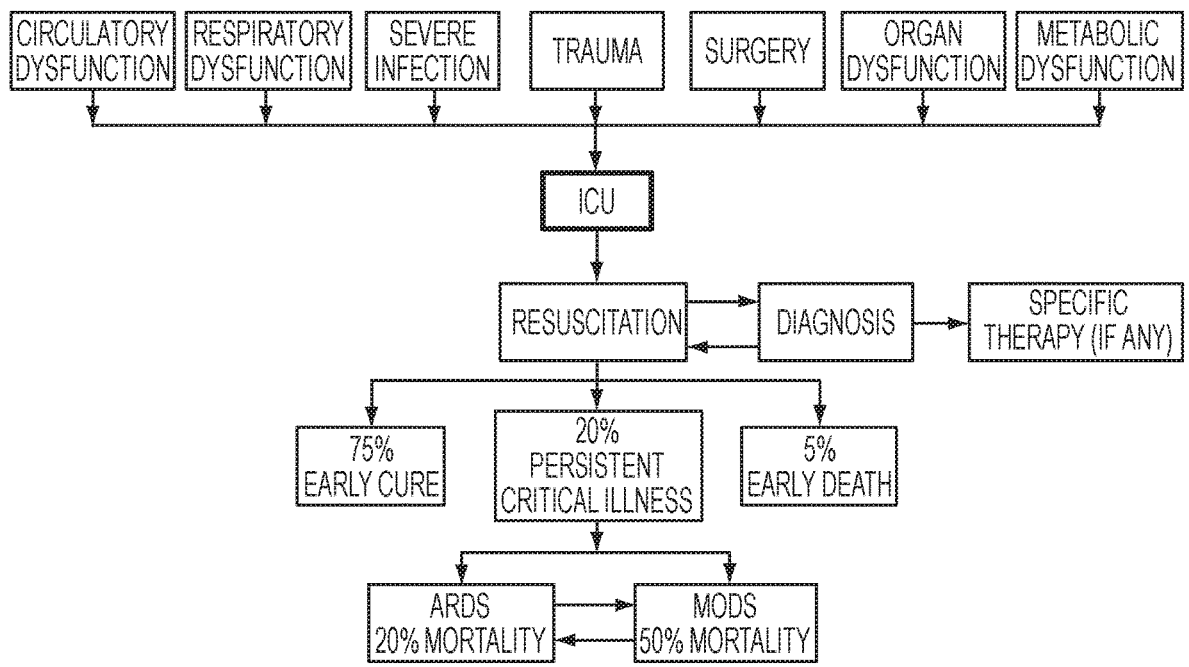
FIG. 1. Pathways of critical illness.

Multiple organ dysfunction syndrome (MODS) is most commonly associated with trauma, sepsis or shock; however a common risk factor appears to be tissue injury (FIG. 1). In addition to trauma and sepsis, the development of MODS/ARDS is associated with a diverse group of clinical scenarios, including pancreatitis, cancer, peritonitis, surgery, acute lung injury, ischemia-reperfusion, radiation, burns, transfusion reactions, and auto-inflammatory disorders. The organs most affected histologically in MODS are in descending order: the lungs, liver, kidney, heart, gut, brain, pancreas and adrenals, though it is likely that most if not all organs are ultimately affected. In addition, disseminated intravascular coagulation is an insidious manifestation of MODS. Endothelial cell death and dysfunction underlies much of the systemic process, resulting in microcirculatory dysfunction and consequent capillary leak, interstitial edema, hemorrhage, and cellular infiltration.

Circulating histones mediate detrimental effects in patients. Recent evidence has suggested that there may be a shared molecular mechanism responsible for the acute lung injury associated with these diverse disorders—and that involves extracellular histones. Eukaryotic genomes are organized in chromatin, a DNA-protein complex whose basic repeating unit is the nucleosome. The nucleosome consists of wrapped around an octamer of histone proteins (two each of histones H2A, H2B, H3, and H4). However, severely injured tissues release large quantities of nucleosomes into the circulation, which are further broken down into individual histones. Elevated levels of circulating histones can be derived either from damaged and apoptotic cells or from the degradation of neutrophil extracellular traps (NETs), which are structures of extracellular histones and DNA that ensnare and kill bacteria. In severely ill patients, an increase in histone levels within 6 hours of admission predicts for mortality. Similarly, in patients with major trauma, circulating histones levels correlate with injury severity, elevated by 4 hours and peaking at about 24 hours after trauma and still detectable at 72 hours. In addition, extracellular histones have been detected in bronco alveolar lavage fluids (BALF) from patients with ARDS but not in BALF from non-ARDS patients. Transfusion-related acute lung injury (TRALI) is the leading cause of death from transfusion therapy in the US. NETs and circulating histone levels are substantially higher in mice and humans with fatal TRALI.

Several lines of evidence have substantiated that circulating histones, not nucleosomes or DNA, mediates these toxic effects. For example, nucleosomes which have been briefly sonicated or exposed to serum (i.e., DNA is degraded and individual histories are released) induce endothelial cell death. Human patient serum with histone levels in excess of 50 µg/ml is toxic to cultured endothelial cells. Intravenous injection of recombinant histones in mice causes endothelial damage, cytokine elevation, platelet aggregation, and microvascular necrosis in the lungs, leading to death.

Extracellular histories mediate tissue damage through multiple mechanisms (FIG. 2) (Chen. R., et al., Release and activity of histone in diseases. Cell Death Dis, 2014, 5: p. e1370). First, histones disrupt cell membranes, resulting in $Ca^{2+}$ influx and subsequent elevations in intracellular $Ca^{2+}$ concentrations and cell damage. In this way, the tissue injury is amplified through release of additional histones into the circulation. Second, histones bind to and activate TLR2 and TLR4, thereby inducing NF-κB and pro-inflammatory cytokine production. Third, histones have been shown to induce a pro-coagulant phenotype in platelets, thereby accelerating blood coagulation and enhancing thrombin generation in a mechanism that involves Toll like receptors (TLR) 2 and 4. Recently, neutrophil extracellular traps were shown to activate platelets leading to thrombosis, and the major contributor to this process was histone H4.8 A fourth mechanism is through increased gut permeability, which allows endotoxin or bacteria to enter the circulation and prime neutrophils. Activated neutrophils then release toxic mediators (i.e., cytokines) to damage lungs and other organs. Consistent with this idea, it has been reported that cytokines, including tumor necrosis factor (TNF)-α, interleukin (IL)-6 and IL-10, are elevated in mice 2 hours after exogenous histone infusion.

Current Attempts to Abrogate Histone-Induced Injury.

Histones represent one of many damage-associated molecular pattern molecules that can initiate and perpetuate immune response; their potential to amplify tissue injury by killing other cells in addition to their agonistic activity on TLRs provides a rationale to target histones for therapy. Unfortunately, approaches currently being pursued in experimental models have marked limitations. First, while TLRs clearly mediate the immune response induced by histones, they have no role in the calcium-mediated cytotoxicity, negating the use of TLR2/4 neutralizing antibodies. Second, several other biologics that demonstrated efficacy in animal models have failed to provide a therapeutic benefit in clinical trials (activated protein C) or have increased risk of bleeding (heparin, APC) or toxicity (histone deacetylase inhibitors). In addition, many biologics require special handling and storage, special dosing considerations, and risk allergic reactions (recombinant proteins and antibodies), which limit their use in situations that are unique to military operations. The development of selective inhibitors of histone-mediated injury is a unique clinical opportunity to interrupt a pathophysiologic cascade responsible for significant morbidity and mortality.

RNA aptamers are single-stranded nucleic acids whose binding properties depend on their sequence and structure.

Aptamers have high binding affinity and specificity with significant advantages over other biologics, including stability at room temperature, resistance to serum degradation, and minimal immunogenicity. Proposed studies will use the in vitro selection technique SELEX (Systemic Evolution of Ligands by Exponential enrichment) to isolate high affinity RNA aptamers against human histories and test efficacy in human pulmonary microvascular endothelial cells and in animal models of histone-mediated ALI.

While aptamers are analogous to antibodies in their range of target recognition and variety of applications, they possess several key advantages over their protein counterparts: (1) they are self-refolding, single-chain, and redox-insensitive, and unlike proteins do not aggregate. They tolerate pH and temperatures that proteins do not. (2) They are easier and more economical to produce. Their production does not depend on bacteria, cell cultures or animals. (5) They can easily be chemically modified to yield improved properties and nuclease resistance for plasma stability (6) Their small size leads to a high number of moles of target bound per gram, and transport properties allowing improved tissue penetration (7) They are much more stable at ambient temperature than antibodies yielding a much higher shelf life, and they can tolerate transportation without any special requirements for cooling, eliminating the need for a continuous cold chain. Another important advantage of aptamers is the feasibility of generating cross-species aptamers that enable testing the same reagent in preclinical animal models and in future human clinical trials. Finally, the clinical potential of aptamers is highlighted by the FDA approval of an aptamer-based drug for macular degeneration and by clinical trials that demonstrate the safety and efficacy of systemically administered RNA.

MODS is described as "the development of potentially reversible physiologic derangement involving two or more organ systems not involved in the disorder that resulted in ICU admission, and arising in the wake of a potentially life-threatening physiologic insult". With the lungs being the organ most commonly involved, acute lung injury (ALI) and acute respiratory distress syndrome (ARDS) may be the primary and most clinically relevant presentation. The annual incidence of ALI/ARDS approximates 200,000 cases in the United States, with mortality approaching 40%. Despite extensive research into the pathogenesis of ALI and clinical trials testing new therapeutics, the improvement in outcomes following ARDS over the past decade are due to improved strategies of mechanical ventilation and advanced support of other failing organs, as there remains no effective pharmacotherapy to treat patients with this syndrome. Furthermore, patients who survive frequently have significant psychological and physical morbidity, residual physical limitations and poor quality of life. The development of ALI/ARDS occurs as a consequence of critical illness of diverse etiologies including initial major trauma, toxic inhalation, burns, near-drowning, radiation, sepsis, and blood transfusion. Furthermore, another common manifestation of MODS is haemostatic abnormalities ranging from subclinical activation of blood coagulation (hypercoagulability) to acute DIC and subsequent consumption of platelets and coagulation proteins causing bleeding.

In response to apoptotic signals, core histones separate from genomic DNA, which results in histone cytoplasmic translocation and subsequent release into the extracellular space. By causing tissue injury (FIG. 2) histones are also involved in a self-sustaining cascade of apoptosis and subsequent histone release. In vivo, histone administration also accelerates cytokine release, endothelial damage, coagulation activation, and lung injury in animal models. Extracellular histones have been implicated in the development of many different disease conditions:

Acute lung injury. Extracellular histones have been detected in Broncho alveolar lavage fluids (BALF) from patients with ARDS but not in BALF from non-ARDS patients.

Transfusion related acute lung injury. Transfusion-related acute lung injury a (TRALI) is the leading cause of death from transfusion therapy in the US. Neutrophil extracellular traps and circulating histone levels are substantially higher in mice and humans with fatal TRALI.

Sepsis. Mice show increased levels of histones in serum after endotoxin administration, H3 and H4 are the major components responsible for this toxicity. Endothelial disruption and consequential coagulation disorders are essential in pathogenesis of sepsis, with 35% of patients with sepsis developing DIC. Changes in the integrity of endothelium are the basis of these severe and mostly fatal complications of sepsis.

Trauma and burns. Histories are released following trauma or severe cellular stress. A cohort study of 52 patients shows that serum histone levels are significantly elevated after severe non-thoracic blunt trauma. Increased serum histones were positively and negatively related to injury severity score and Glasgow Coma Score, respectively High serum histone levels positively correlate with severe complications and poor prognosis.

Ischemia/reperfusion and drug-mediated tissue injury result in sterile inflammation. Serum histone levels are significantly elevated in animal models with liver, kidney, and brain injury, suggesting an important role of histones in the regulation of sterile inflammation. Indeed, circulating histones are major mediators of animal death in several liver injury models including concanavalin A-triggered liver injury, acetaminophen-induced hepatotoxicity, liver I/R, and acute liver failure. Extracellular histories function as damage-associated molecular patterns (DAMPs) and mediate sterile inflammation and organ damage.

Coagulation and thrombosis. Histone administration in mice increases platelet aggregation and subsequent platelet-dependent thrombin formation and microvascular thrombosis. Of them, H4 has the strongest impact on platelet activity. Histones also induce a procoagulant phenotype in human platelets, which enhance thrombin generation and accelerate the blood clotting process. Exogenous histories dose dependently increase plasma thrombin generation in the presence of thrombomodulin.

Autoimmune and auto-inflammatory disorders. Histone release from NETosis has been implicated in a number of autoimmune and auto-inflammatory diseases such as rheumatoid arthritis, systemic lupus, small-vessel vasculitis.

Cerebral infarct. High concentrations of serum nucleosomes are detected in patients with cerebral stroke, especially in patients with large infarction volumes. Serum nucleosome levels rise quickly after post-ischemia, peak at days 3-5, and then fall slowly.

Cancer. Higher concentrations of circulating nucleosomes occur in tumor entities that are highly active or that are detected at advanced stages. An increase in baseline values of circulating histones indicated disease progression, whereas a decrease of the baseline values was an indicator of disease regression.

Ebola and related viral infections. Ebola virus is very pathogenic in humans and induces an acute hemorrhagic fever that leads to death in about 70% of patients. Viral hemorrhagic fever (VHF) is a severe febrile illnesses caused by enveloped RNA viruses from 4 taxonomic families: Arenaviridae, Bunyaviridae, Filoviridae, and Flaviviridae. As the disease progresses, vascular damage with capillary leakage may cause nondependent edema and serous effusions of body cavities such as the pleural and peritoneal spaces. Hemorrhages occur when the patient has thrombocytopenia or severe platelet dysfunction. The extensive multifocal necroses in filoviral infections are probably caused, at least in part, by ischemia associated with fibrin thrombi caused by disseminated intravascular coagulation. The lysis of Ebola-infected cells such as monocytes and macrophages may partially account for cell death. The massive fragmentation of DNA found in the blood and apoptosis vas observed early during disease in all fatalities studied, whereas hemorrhagic signs were observed only in some terminal patients.

Development of RNA aptamers to human histones H3 and H4. The goal of these studies is to identify RNA aptamers that selectively bind with high affinity to both human histones H3/H4. An RNA library of $10^{12}$ RNA sequences (with 2'-fluoro modified pyrimidines) consisting of 51 nucleotide-long, RNA oligonucleotides that include a random region of 20 nucleotides and two constant flanking regions of known sequence (these enable PCR amplification at each selection round). For the first round of selection, the RNA library is pre-cleared against control proteins BSA and human IgG to remove nonspecific binders and removed by capturing the RNA-protein complexes onto a Centrex nitrocellulose centrifugal filter (high protein/low nucleic acid binding filter). Those RNAs that do not bind BSA or human IgG (flow-through after filtering) are collected and incubated with commercially available recombinant human histone H3. The RNA aptamers that bind to histone H3 are captured onto a second Centrex nitrocellulose centrifugal filter, eluted off the filter with chloroform and extracted. The RNA aptamers are then amplified for the next round of selection with RT-PCR using primers specific to the flanking constant regions of the RNA library followed by in vitro transcription via a T7 promoter included in the 5'-PCR primer. For round two of the selection, the pool of RNA derived from round one is pre-incubated with BSA and human IgG for the counter-selection step and the flow-through, containing RNAs that do not bind BSA or human IgG, incubated with commercially available recombinant human histone H4. Those RNAs that bind histone H4 are eluted and amplified as described above. Selection alternates between human historic H3 and H4 for several rounds in order to isolate aptamers that bind to both of these proteins. High affinity aptamers are enriched by modifying the selection conditions (e.g. increasing the RNA:histone ratio during the positive selection step and reducing the incubation time of aptamers with histones H3/H4). The progress of the selection is assessed by determining the sequence diversity of the random regions from round to round by high-throughput sequencing (HTS) and identifying sequence and structure families using bioinformatics analyses. Progress of the selection is assessed by carrying out standard in vitro binding assays (e.g. double-filter nitrocellulose filter binding assays or surface plasmon resonance measurements) with the pools of RNA from each round.

Characterization of individual aptamer sequences. Individual RNA aptamers identified from the sequence analysis are screened for (1) specificity of binding and for (2) ability to inhibit histone activity. In vitro filter binding assays are performed with the top 10-15 sequences from the HTS and bioinformatics analysis. Radiolabeled aptamers re incubated with varying amounts of control proteins (BSA and human IgG) or historic H3 or H4 proteins for 5 min prior to loading onto a dot-blot apparatus. Aptamers bound to histone proteins are retained onto the nitrocellulose filter while unbound aptamers will be retained onto the nylon filter. Membrane filters are quantified using a phospho imager screen and a corrected fraction bound will be determined for each aptamer. Binding specificity is assessed by determining background binding of each aptamer to control proteins (BSA and IgG). A more extensive quantitative determination of binding affinities via surface plasmon resonance is reserved for the 5 aptamers that demonstrate the greatest affinity and specific binding in the filter binding assays. For this work, biotin is coupled to the aptamers during chemical synthesis then immobilized on streptavidin-coupled chips using standard protocols. Recombinant human histone H3 and H4 proteins are injected over the sensor surface for 5 min (association and dissociation time). Various concentrations of histone proteins are injected by serially diluting samples. Concentrations are adjusted based on the binding signal response to obtain optimal affinity determinations. The selectivity studies are carried out by injecting comparable concentrations of several control proteins (i.e. BSA and human IgG) over the immobilized aptamers. The dissociation constant ($K_D$) for each aptamer is calculated by global fitting of four concentrations of histone proteins, assuming a constant density of aptamers on the surface of the chip. A 1:1 binding mode with mass transfer fitting is used to obtain the kinetic data. BSA and human IgG measurements are aligned to histone H3 and H4 data for the non-specific analysis.

Assess functional efficacy of histone specific RNA aptamers. These studies test the ability of the RNA aptamers to neutralize the toxic effects of histories in vitro and in vivo. The best two candidate aptamers that selectively bind H3/H4 in the low pM-low nM range as determined above are used in these studies. Mutated aptamers that do not bind histones serve as negative control aptamers. These studies utilize chemically synthesized aptamers to maximize reproducibility, serum stability, and prevent immune activation. To model circulating histone content, human pulmonary microvascular endothelial cells (EC) or C57Bl/6 mice re exposed to histones purified from calf thymus (contains a heterogenous mixture of core histories) in the presence or absence of aptamer. Human patient serum with historic levels in excess of 50 µg/ml is toxic to EC2; therefore this concentration is used in vitro. Dose response curves for the aptamers are determined in vitro and define the concentration used in in vivo studies.

Endothelial cell culture: Endothelial monolayers are treated with histones (50 µg/ml) with and without one of three aptamers (negative binding, 2 histone binding) at varying aptamer concentrations, based on the $K_D$ for each aptamer determined above (typical range is 1 nm-100 nm). Cells also receive aptamers without histones as a control. The following measurements are made: Measurement of calcium influx. Intracellular calcium concentration is measured using established protocols with fura 2-AM as the fluorescent probe.

Measurement of TLR activation. Expression of IFN-γ, IL-1β, IL-6, and TNF-α by RT-PCR.

Detection of cell toxicity. Live, apoptotic and dead cells are determined by flow cytometry following staining with annexin-V and propidium iodide.

Platelet activation: Blood is collected from human volunteers, platelet-rich plasma prepared, and platelets isolated. Using the histone and aptamer treatment protocol described above, studies are performed in a collagen-coated flow chamber perfused with washed human platelets. The surface area covered by platelet aggregates is quantified. Shear stress conditions are adjusted to replicate the values for arterial (~20 dynes/cm$^2$) or venous shear stress (~3 dynes/cm$^2$). In separate studies, platelet surface marker expression (activated α2bβ3 and P-selectin) are detected by fluorescent antibodies followed by flow cytometry.

Animal model. The best evidence of whether ALI has occurred in an animal is provided by a measurement of the cellular response (such as neutrophil counts in the BALF), a measurement of the integrity of the alveolar capillary barrier (such as movement of high molecular weight proteins from the serum into the airspaces) and histological images showing lung injury. Histones are injected into the tail vein of C57BL/6 mice (50 mg/kg body weight). The two aptamers identified in the in vitro experiments that are most effective and have greatest binding are tested. Animals are pretreated with a control aptamer or one of the two histone aptamers (1 mg/kg or 5 mg/kg, IV) 10 minutes prior to histone administration. These two doses of aptamers represent "low" and "high" doses and are adjusted as indicated on the binding data obtained above. In separate experiments, aptamers are administered at various times after delivery of the histones (5, 15, and 30 minutes) to examine the ability of the aptamer to prevent injury after histone release. Non-invasive determination of respiratory function (reduced O2 saturation) is continuously monitored using a pulse oximeter. After 3 hours (or at the time of death if occurs prior to 3 hours) the mice are killed and the following performed:

TLR activation Blood is collected and serum isolated, and stored at −80° C. Cytokines/chemokines are all quantified using a customized multiplex magnetic bead panel kit.

Alveolar permeability and inflammation: Tracheas are isolated and cannulated and the lungs flushed with sterile PBS. Cytospins of BALF cells are stained with modified Wright-Giemsa. Alveolar permeability is assessed by quantitative detection of mouse albumin in BALF by ELISA.

Lung histology. Lungs are fixed in 4% (w/v) paraformaldehyde for 24 h and embedded and sectioned. Sections are stained with hematoxylin and eosin (H&E) and Mallory's phosphotungstic acid-hematoxylin staining for fibrin then examined by a pathologist for evidence of neutrophils in alveolar spaces, capillary congestion, intra-alveolar hemorrhage, fibrin deposits and thrombi.

Statistical analysis. All data is expressed as mean±SEM. Statistical analysis is carried out using computer software SYSTAT. Results are analyzed using paired and unpaired t-tests for comparisons between two groups. For multiple comparisons, mixed model of ANOVA is employed to compare different treatment groups. Differences between mean values of multiple groups are analyzed with a Newman-Keuls post-hoc test. Differences are considered statistically significant at p values of <0.05.

Animals: The ARRIVE (Animal Research: Reporting In Vivo Experiments) guidelines have been reviewed and are followed for reporting of research findings. Studies are performed in male and female C57BL/6 mice (~10 wks of age), using the minimum number of mice required to address the described protocols. For the animal studies, a power analysis assuming a 25% difference between the control and treatment groups with a standard deviation of 20% for both groups, an alpha error level of 5% (two sided) and a beta error level of 50% indicates a sample size of 8 mice for each study group and for each protocol. Based on these estimates it is estimated that a total of approximately 192 mice (3 aptamers×4 time points×2 doses) are needed to complete the study. Prior to collection of tissues, the mice are euthanized by a barbiturate overdose.

Humans: Healthy individuals (>18 years of age, 50% males) who are not pregnant are recruited from laboratory personnel to donate venous blood for the isolation of platelets. The population recruited reflects the race and ethnic composition of the community. The potential risks of phlebotomy are limited to local pain and local hematoma. Multiple experimental groups are studied from a single 10 ml blood draw.

Aptamer Portion

The present technology uses nucleic acid aptamer constructs that have been created to specifically inhibit the human H3 and H4 histones. In certain embodiments, the constructs are chemically modified (2'-fluoropyridines) RNA constructs making them nuclease resistant. See WO 2010/019446, which is incorporated by reference in its entirety. In certain embodiments the aptamers are RNA. RNA aptamers have the following characteristics: (1) RNA aptamer libraries have a higher structural complexity as compared to DNA aptamer libraries (most DNA aptamers form predictable and similar G-quadruplex structures), thereby increasing the likelihood of identifying aptamers with the desired properties; and (2) RNA chemistries to increase serum stability and safety have been more extensively evaluated for in vivo applications. In certain embodiments, DNA aptamers are used.

Aptamers are single stranded oligonucleotides that can naturally fold into different 3-dimensional structures, which have the capability of binding specifically to biosurfaces, a target compound or a moiety. The term "conformational change" refers to the process by which a nucleic acid, such as an aptamer, adopts a different secondary or tertiary structure. The term "fold" may be substituted for conformational change.

Aptamers have advantages over more traditional affinity molecules such as antibodies in that they are very stable, can be easily synthesized, and can be chemically manipulated with relative ease. Aptamer synthesis is potentially far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These characteristics of aptamers make them attractive for diagnostic applications.

Aptamers are typically oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified, nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonmethyluracil; 5-methoxyuracil; 2-methythio-N6-isopentyladenine; uracil-5-oxyacetic acid methyl ester, psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine 5-ethyluracil; 5-ethylcytosine; 5-butyluracil; 5-pentyluracil; 5-pentylcytosine; and 2,6-diaminopurine; methylpsuedouracil; 1-methylguanine; 1-methylcytosine.

In certain embodiments, aptamer modifications include: (a) Nucleotides modified by replacing the 2' position with either a fluoro-(F), amino-($NH_2$) or O-methyl ($OCH_3$) group for enhanced nuclease resistance. These modified nucleotides are introduced either chemically or enzymatically. (b) Bridging phosphorothioates incorporated enzymatically. (c) End caps that involve reversing the polarity of the chain incorporated during chemical synthesis. (d) Linkers inserted at the 5'-ends of aptamers by either chemical or enzymatic means to provide handles for conjugation or to alter pharmacokinetic properties. Keefe et al., *Aptamers as therapeutics*, Nat Rev Drug Discov. 2010 July; 9(7):537-50.

In certain embodiments, modification of the 2'-position of the ribose indirectly improves nuclease resistance of the internucleotide phosphate bond and at the same time increases duplex stability ($T_m$), and also provides protection from immune activation, 2'-O-methyl RNA (2'OMe) is a naturally occurring RNA variant found in mammalian ribosomal RNAs and transfer RNAs. It is nontoxic and can be placed within either the S or AS strands of a siRNA. Heavy modification with 2'OMe RNA can reduce potency or completely inactivate a siRNA; alternating 2'OMe with RNA bases generally retains siRNA function while conferring significant nuclease stabilization. 2'OMe RNA can be combined with other 2'-modifications which are not naturally occurring bases with good results. Behlke, *Chemical Modification of siRNAs for in Vivo Use*, Oligonucleotides 18:305-320 (2008).

The 2'-fluoro (2'-F) modification is compatible with siRNA function and also helps stabilize the duplex against nuclease degradation. Incorporation of 2'-F at pyrimidine positions maintains siRNA activity in vitro and in vivo. The 2'-F modification is even tolerated at the site of Ago2 cleavage. The combined use of 2'-F pyrimidines with 2'OMe purines can results in RNA duplexes with extreme stability in serum and improved in vivo performance. The 2'-O-(2-methoxyethyl) RNA (MOE) modification has been extensively used in antisense oligonucleotides and confers significant nuclease stability to an oligonucleotide as well as increases $T_m$. 2'-MOE residues can be incorporated into siRNAs much like 2'OMe or 2'-F, however this modification is not generally available for use. The 2-fluoro-β-D-arabinonucleotide (FANA) modification has also shown promise in antisense oligonucleotide applications and can also be placed in siRNAs. Substitution of FANA for RNA in the entire S-strand confers significant stabilization to nucleases while maintaining functional potency of the duplex; however, the AS-strand is less tolerant of the FANA modification. Locked nucleic acids (LNAs) contain a methylene bridge which connects the 2'-O with the 4'-C of the ribose. The methylene bridge "locks" the sugar in the 3'-endo conformation, providing both a significant increase in $T_m$ as well as nuclease resistance. Extensive modification of a siRNA with LNA bases generally results in decreased activity (even more so than 2'OMe); however, siRNAs with limited incorporation retain functionality and offer significant nuclease stabilization.

The aptamers of the invention are synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Certain embodiments of the present invention provide a nucleic acid molecule of not more than 90 nucleotides in length comprising an aptamer, wherein the aptamer specifically targets extracellular histones. In certain embodiments of the present invention, the aptamer portion is specific for human histones H3 and/or H4.

In certain embodiments, the aptamer comprises at least 90% identity to an RNA sequence listed in Table 1. In certain embodiments, the aptamer comprises at least 95% identity to an RNA sequence listed in Table 1. In certain embodiments, the aptamer comprises 100% identity to an RNA sequence listed in Table 1.

In certain embodiments, the aptamer specifically targets human H3 and H4. In certain embodiments, the aptamer comprises at least 90% identity to KU1, KU2 or KU3. In certain embodiments, the aptamer comprises at least 95% identity to KU1, KU2 or KU3. In certain embodiments, the aptamer has 100% identity to KU1, KU2 or KU3.

In certain embodiments, the aptamer specifically targets human H3. In certain embodiments, the c aptamer comprises at least 90% identity to KU7, KU8 or KU9. In certain embodiments, the aptamer comprises at least 95% identity to KU7, KU8 or KU9. In certain embodiments, the aptamer has 100% identity to KU7, KU8 or KU9.

In certain embodiments, the aptamer specifically targets human H4. In certain embodiments, the aptamer comprises at least 90% identity to KU4, KU5 or KU6. In certain embodiments, the aptamer comprises at least 95% identity to KU4, KU5 or KU6. In certain embodiments, the aptamer has 100% identity to KU4, KU5 or KU6.

In certain embodiments, additional modifications are made to the aptamer portion. Additional modifications to the aptamer portion include 2'O-methyl modification of the pyrimidines. In other embodiments, all of the nucleotides in the aptamer are 2'O-methyl modified. Alternatively, the pyrimidines, or all the nucleotides, may be modified with 2'fluoros (both pyrimidines and purines). Additional modifications to the nucleotides in the aptamer include large molecular weight conjugates like PEGylation, lipid-based modifications (e.g., cholesterol) or nanoparticles PEI or chitosan) to improve the pharmacokinetic/dynamic profile of the chimera.

Small Molecule Portion

In certain embodiments, the aptamers are linked to other molecules in order to improve clearance (pharmacokinetics and pharmacodynamics). In certain embodiments, the other molecules include PEG, cholesterol or other lipid, nanoparticles. The aptamers of the present invention can be operably linked to one or more small molecule entities. In certain embodiments, the entity is a fluorescent tag, affinity tag, a protein, a solid substrate, a cell surface, or a cellular component. In certain embodiments, the cellular component is a cell wall or cell membrane. In certain embodiments, the solid substrate is a component of silica, cellulose, cellulose acetate, nitrocellulose, nylon, polyester, polyethersulfone, polyolefin, or polyvinylidene fluoride, or combinations thereof. In certain embodiments, the solid substrate is a stent or other medical device, filter, magnetic bead, metal oxide, latex particle, microtiter plates, polystyrene bead, or CD-ROM.

In certain embodiments, the aptamer is linked to the entity by means of a linker. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin. In certain embodiments, the aptamer is linked to the entity by means of a covalent bond.

The entity, for example, may additionally or alternatively, be a detection means. A number of "molecular beacons" (such as fluorescence compounds) can be attached to aptamers to provide a means for signaling the presence of and quantifying a target chemical or biological agent. Other exemplary detection labels that could be attached to the aptamers include biotin, any fluorescent dye or tracer, amine modification, horseradish peroxidase, alkaline phosphatase, etc.

In certain embodiments, the aptamer is operably linked to a detection means and to a solid substrate. For example, the aptamer may be linked to a fluorescent dye and to a magnetic bead.

In certain embodiments, the small molecules are biologic or pharmacologic agents that can inhibit H3 and/or H4 histones.

Linking Molecules

Chemistries that can be used to link molecules to the aptamer are known in the art, such as disulfide linkages, amino linkages, covalent linkages, etc. Additional linkages and modifications can be found on the world-wide-web at trilinkbiotech.com/products/oligo/oligo_modifications.asp.

Non-Aptamer Therapeutic Agents and Diagnostic Labels

Other non-antibody therapeutic agents targeted against either histones or downstream effectors of a historic mediated pathway may also be utilized in combination with anti-histone antibodies or fragments thereof, administered either before, simultaneously with, or following administration of one or more anti-histone antibodies or fragments thereof. Various therapeutic agents of use in treating histone associated disease states are known in the art, such as activated protein C (APC), thrombomodulin, a peptide fragment of histone H1, H2A, H2B, H3 or H4, granzyme A, granzyme B, plasmin, Factor 7-activating protease, heparin, and any such known agent may be utilized in combination with the subject anti-histone antibodies or antibody fragments. A human histone H4 peptide may comprise residues 50-67 or 40-78 of human H4 (see, e.g., U.S. Publ. No. 20090117099).

In certain embodiments, the therapeutic agent is selected from the group consisting of an antibody, an antibody fragment, an immune conjugate, a radionuclide, an immunomodulatory, an anti-angiogenic agent, a pro-apoptotic agent, a cytokine, a chemokine, a drug, a toxin, a hormone, an siRNA, a cytokine, a chemokine, a coagulation inhibitor, a stem cell growth factor, a lymphotoxin, a hematopoietic factor, a colony stimulating factor, an interferon, erythropoietin, thrombopoietin, an enzyme, recombinant human thrombomodulin and activated human protein C.

In certain embodiments, the antibody, antibody fragment or immune conjugate binds to an antigen selected from the group consisting of histone H2B, histone H3, histone H4, a proinflammatory effector of the innate immune system, a proinflammatory effector cytokine, a proinflammatory effector chemokine, a target specifically associated with infectious disease, acute respiratory distress syndrome, septicemia, septic shock, GVHD, transplant rejection, atherosclerosis, asthma, granulomatous disease, a neuropathy, cachexia, a coagulopathy, acne, giant cell arteritis or myocardial ischemia, TNF-α, MIF, CD74, HLA-DR, IL-1, IL-3, IL-4, IL-5, IL-6, IL-8, IL-12, IL-15, IL-17, IL-18, IL-23, IL-4R, IL-6R, IL-13R, IL-15R, IL-17R, IL-18R, CD40L, CD44, CD46, CD55, CD59, CCL19, CCL21, mCRP, MCP-19, MIP-1A, MIP-1B, RANTES, ENA-78, IP-10, GRO-β, lipopolysaccharide, lymphotoxin, HMGB-1, tissue factor, a complement regulatory protein, a coagulation factor, thrombin, a complement factor, C3, C3a, C3b, C4a, C4b, C5a, C5b Flt-1 and VEGF.

In certain embodiments, the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine, a vinca alkaloid, a tyrophostin, canertinib, dasatinib, erlotinib, gefitinib, imatinib, lapatinib, leflunomide, nilotinib, pazopanib, semaxinib, sorafenib, sunitinib, sutent, vatalanib, PCI-32765 (ibrutinib), PCI-45292, GDC-0834, LFM-A13 and RN486.

In certain embodiments, the toxin is selected from the group consisting of ricin, abrin, alpha toxin, saporin, ribonuclease (RNase), e.g., onconase, DNase 1, *Staphylococcal* enterotoxin-A, pokeweed antiviral protein, gelonin, diphtheria toxin, *Pseudomonas* exotoxin, and *Pseudomonas* endotoxin.

In certain embodiments, the immunomodulatory is selected from the group consisting of a cytokine, a stem cell growth factor, a lymphotoxin, a hematopoietic factor, a colony stimulating factor (CSF), an interleukin (IL), erythropoietin, thrombopoietin, tumor necrosis factor (TNF), granulocyte-colony stimulating factor (G-CSF), granulocyte macrophage-colony stimulating factor (GM-CSF), interferon-α, interferon-β, interferon-γ, interferon-λ, TGF-α, TGF-β, interleukin-1 (IL-1), IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, FLT-3, angiostatin, thrombospondin, recombinant human thrombomodulin, endostatin and lymphotoxin.

In certain embodiments, the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-1, insulin-like growth factor-II, erythropoietin (EPO), osteoinductive factors, interferon-α, interferon-β, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

In certain embodiments, the radionuclide is selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$I, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Ru, $^{149}$Pm, $^{169}$Er, $^{194}$Ir, $^{58}$Co, $^{80m}$Br, $^{99m}$Tc, $^{103m}$Rh, $^{109}$Pt, $^{119}$Sb, $^{125}$I, $^{189m}$Os, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br, $^{169}$Yb and $^{227}$Th.

Amplification Methods

In one embodiment of the present invention, the method involves the amplification of selected RNAs. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. In one embodiment of the present invention, at least one type of aptamer is immobilized on a solid surface.

According to the methods of the present invention, the amplification may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159 and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Diagnostic techniques that are useful in the methods of the invention include, but are not limited to direct DNA sequencing, pulsed-field gel electrophoresis (PFGE) analysis, allele-specific oligonucleotide (ASO), dot blot analysis and denaturing gradient gel electrophoresis, and are well known to the artisan.

The sample may be contacted with the aptamer in any suitable manner known to those skilled in the art. For example, the sample may be solubilized in solution, and contacted with the aptamer by solubilizing the aptamer in solution with the sample under conditions that permit binding. Suitable conditions are well known to those skilled in the art. Alternatively, the sample may be solubilized in solution with the aptamer immobilized on a solid support, whereby the sample may be contacted with the aptamer by immersing the solid support having the aptamer immobilized thereon in the solution containing the sample.

General Terminology

"Synthetic" aptamers are those prepared by chemical synthesis. The aptamers may also be produced by recombinant nucleic acid methods. "Recombinant nucleic molecule" is a combination of nucleic sequences that are joined together using recombinant nucleic technology and procedures used to join together nucleic sequences known in the art.

A "therapeutic agent" is an atom, molecule, or compound that is useful in the treatment of a disease. Examples of therapeutic agents include antibodies, antibody fragments, peptides, drugs, toxins, enzymes, nucleases, hormones, immune modulators, antisense oligonucleotides, small interfering RNA (siRNA), chelators, boron compounds, photoactive agents, dyes, and radioisotopes. An "antibody" as used herein refers to a full-length (i.e., naturally occurring or formed by normal immunoglobulin gene fragment recombinatorial processes) immunoglobulin molecule (e.g., an IgG antibody). AD "antibody" includes monoclonal, polyclonal, bispecific, multispecific, murine, chimeric, humanized and human antibodies. An "antibody fragment" is a portion of an intact antibody such as $F(ab')_2$, $F(ab)_2$, Fab', Fab, Fv, st, scFv, dAb and the like. Regardless of structure, an antibody fragment binds with the same antigen that is recognized by the full length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb). Fragments of antibodies that do not bind to the same antigen as the intact antibody, such as the Fe fragment, are not included within the scope of an "antibody fragment" as used herein. In certain embodiments, the antibody is an anti-histone antibody (see, e.g., US 2014/0234209, which is incorporated by reference herein).

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An anti-histone aptamer, antibody or antibody fragment, or a composition described herein, is said to be administered in a "therapeutically effective amount" if the amount administered is physiologically significant. An agent is physiologically significant if its presence results in a detectable change in the physiology of a recipient subject. In particular embodiments, an aptamer, antibody or antibody fragment preparation is physiologically significant if its presence invokes an antitumor response or mitigates the signs and symptoms of an autoimmune disease state. A physiologically significant effect could also be the evocation of a humoral and/or cellular immune response in the recipient subject leading to growth inhibition or death of target cells.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine car pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

As used herein, "sequence identity" or "identity" in the context of two nucleic acid sequences makes reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 86%, 87%, 88%, or 89%; at least 90%, 91%, 92%, 93%, or 94% or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

As noted above, another indication that two nucleic acid sequences are substantially identical, is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching, thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide. 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably hound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

As used herein, the term "derived" or "directed to" with respect to a nucleotide molecule means that the molecule has complementary sequence identity to a particular molecule of interest.

"Treating" as used herein refers to ameliorating at least one symptom of, curing and/or preventing the development of a disease or a condition.

The terms "protein," "peptide" and "polypeptide" are used interchangeably herein.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing, animal models or other test systems, which are well known to the art.

Administration of the aptamer chimera may be accomplished through the administration of the nucleic acid molecule. Pharmaceutical formulations, dosages and routes of administration for nucleic acids are generally known in the art.

The present invention envisions treating a disease, for example, vascular stenosis, restenosis or stroke, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. The formulations may, where appropriate, be conveniently presented in discrete unit dosage forms and may be prepared by any of the methods well known to pharmacy. Such methods may include the step of bringing, into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

Example 1

The incidence of multiple organ dysfunction syndrome (MODS) and the related acute respiratory distress syndrome (ARDS) in critically ill patients is as high as 25% with a mortality of more than 40%. Those patients that do survive often have significant morbidity and prolonged hospitalization and the associated financial burdens. There are several etiologies of MODS/ARDS including trauma, sepsis, burns, ischemia/reperfusion, and acute lung injury (ALI). However, even with identification of high risk patients, there are no effective treatments to prevent the development of these syndromes.

The hypothesis that extracellular histones mediate tissue injury is a relatively new concept. Histones represent one of many damage-associated molecular pattern molecules that can initiate and perpetuate immune response. Their potential to amplify tissue injury by killing other cells, in addition to their agonistic activity on TLRs, provides strong rationale to target histones for therapy. Since histories (cationic proteins) normally associate with DNA in the nucleosome, oligonucleotides (anionic molecules) have extraordinarily high affinity and specificity for histones, making them the preferred reagent for binding and neutralizing circulating histones. RNA aptamers are designed to selectively target and neutralize circulating histones. RNA aptamers are single-stranded oligonucleotides whose binding properties depend on their sequence and structure. Aptamers have significant advantages over other biologics, including stability at room temperature, resistance to serum degradation, and minimal immunogenicity. By using chemically modified RNA, the aptamers are protected from serum degradation and immunogenicity.

Furthermore, alternative approaches to inhibit histone-mediated cellular injury have major limitations. First, while TLRs clearly mediate the immune response induced by histories, they have no role in histone dependent, calcium-mediated cytotoxicity, negating the use of TLR neutralizing antibodies. Second, several other biologics that demonstrate efficacy in animal models have tailed to provide a therapeutic benefit in clinical trials or have increased risk of bleeding or toxicity. In addition, many biologics require special handling and storage, special dosing considerations, and risk allergic reactions (e.g. recombinant proteins and antibodies). The development of RNA aptamer inhibitors of histone-mediated injury is a unique clinical opportunity to interrupt a self-propagating cascade responsible for significant morbidity and mortality.

MODS is described as "the development of potentially reversible physiologic derangement involving two or more organ systems not involved in the disorder that resulted in ICU admission, and arising in the wake of a potentially life-threatening physiologic insult". (Holzheimer R G, Mannick J A, Marshall J C. The multiple organ dysfunction syndrome. 2001) With the lungs being the organ most commonly involved, acute lung injury (ALI) and acute respiratory distress syndrome (ARDS) may be the primary and most clinically relevant presentation. The annual incidence of ALI/ARDS approximates 200,000 cases in the United States, with mortality approaching 40%. (Bosmann M, Grailer J J, Ruemmler R, Russkamp N F, Zetoune F S, Sarma J V, Standiford T J, Ward P A. Extracellular histones are essential effectors of c5ar- and c512-mediated tissue damage and inflammation in acute lung injury. *The FASEB Journal*, 2013; 27:5010-5021). Despite extensive research into the pathogenesis of ALI and clinical trials testing new therapeutics, the improvement in outcomes following ARDS over the past decade are due to improved strategies of mechanical ventilation and advanced support of other failing organs, as there remains no effective pharmacotherapy to treat patients with this syndrome. Furthermore, patients who survive frequently have significant psychological and physical morbidity, residual physical limitations and poor quality of life. The development of ALI/ARDS occurs as a consequence of critical illness of diverse etiologies including initial major trauma, toxic inhalation, burns, near-drowning, radiation, sepsis, and blood transfusion. Furthermore, another common manifestation of MODS is haemostatic abnormalities ranging from subclinical activation of blood coagulation (hypercoagulability) to acute disseminated intravascular coagulation (DIC) and subsequent consumption of platelets and coagulation proteins causing bleeding.

Recent evidence suggests that there may be a shared molecular mechanism responsible for the self-propagating tissue injury associated with these diverse conditions when they progress to MODS, and that involves extracellular histones. Eukaryotic genomes are organized in chromatin, a DNA-protein complex whose basic repeating unit is the nucleosome. The nucleosome consists of DNA wrapped around an octamer of histone proteins (two each of histones H2A, H2B, H3, and H4). (Allam R, Kumar S V, Darisipudi M N, Anders H-J. Extracellular histones in tissue injury and inflammation. *Journal of Molecular Medicine.* 2014; 92:465-472). However, severely injured tissues release large quantities of nucleosomes into the circulation, which are further broken down into individual histones. Elevated levels of circulating histones can be derived either from damaged and apoptotic cells or front the degradation of neutrophil extracellular traps (NETs), which are structures of extracellular histones and DNA that ensnare and kill bacteria. (Thomas G M, Carbo C, Curtis B R, Martinod K, Mazo I B, Schatzberg D, Cifuni S M, Fuchs T A, von Andrian U H, Hartwig J H. Extracellular DNA traps are associated with the pathogenesis of trali in humans and mice. *Blood,* 2012; 119:6335-6343). In critically ill patients, an increase in histone levels within 6 hours of admission predicts mortality. Similarly, in patients with major trauma, circulating histones levels correlate with injury severity, are elevated by 4 hours and peak at about 24 hours after trauma and are still detectable at 72 hours. (Abrams S T, Zharig N, Manson J, Liu T, Dart C, Baluwa F, Wang S S, Brohi K, Kipar A, Yu W. Circulating histones are mediators of trauma-associated lung injury. *American journal of respiratory and critical care medicine.* 2013; 187:160-169).

The present invention provides a therapeutic to rapidly neutralize circulating histones and terminate the self-propagating cycle of tissue injury and development of MODS/ARDS. As indicated by its function in the nucleosome, the ideal reagent to bind histones (highly cationic proteins) is an oligonucleotide (anionic DNA or RNA molecule). An innovative technology is used to identify short oligonucleotides (RNA aptamers) that selectively bind to histones known to cause MODS/ARDS. Since histones are highly conserved across species from yeast to humans, the bio-reagents developed and validated are quickly advanced for testing in preclinical models and human clinical trials.

Several lines of evidence have substantiated that circulating histones, not nucleosomes or DNA, mediate these toxic effects. For example, nucleosomes which have been briefly sonicated or exposed to serum (i.e., DNA is degraded and individual histones are released) induce endothelial cell death. (Allam R, Kumar S V, Darisipudi M N, Anders H-J. Extracellular histones in tissue injury and inflammation. *Journal of Molecular Medicine,* 2014; 92:465-472). Human patient serum with histone levels in excess of 50 µg/ml is toxic to cultured endothelial cells. (Abrams S T, Zhang N, Manson J, Liu T, Dart C, Baluwa F, Wang S S, Brohi K, Kipar A, Yu W. Circulating histones are mediators of trauma-associated lung injury. *American journal of respiratory and critical care medicine,* 2013; 187:160-169). Intravenous injection of recombinant histones in mice causes endothelial damage, cytokine elevation, platelet aggregation, and microvascular necrosis in the lungs, leading to death. (Abrams S T, Zhang N, Manson J, Liu T, Dart C, Baluwa F, Wang S S, Brohi K, Kipar A, Yu W. Circulating histones are mediators of trauma-associated lung injury. *American journal of respiratory and critical care medicine,* 2013; 187:160-169; Xu J, Zhang X, Pelayo R, Monestier M, Ammollo C T, Semeraro F, Taylor F B, Esmon N L, Lupu F, Esmon C T, Extracellular histones are major mediators of death in sepsis. *Nature medicine,* 2009; 15:1318-1321). Extracellular histones mediate tissue damage through multiple mechanisms including: (1) disruption of cell membranes, resulting in $Ca^{2+}$ influx and subsequent elevations in intracellular $Ca^{2+}$ concentrations and cell damage; (2) activation of TLR2 and TLR4, thereby inducing NF-κB and pro-inflammatory cytokine production; (3) induction of a pro-coagulant phenotype in platelets, thereby accelerating blood coagulation and enhancing thrombin generation in a mechanism that involves Toll like receptors (TLR) 2 and 4 (Semeraro F, Ammollo C T, Morrissey J H, Dale G L, Friese P, Esmon N L, Esmon C T. Extracellular histones promote thrombin generation through platelet-dependent mechanisms: Involvement of platelet tlr2 and tlr4. *Blood,* 2011; 118:1952-1961); (4) increased gut permeability, which allows endotoxin or bacteria to enter the circulation and prime neutrophils which, in turn, release toxic mediators (i.e., cytokines) to damage lungs and other organs.

Current attempts to abrogate histone-induced injury have limitations. Histories represent one of many damage-associated molecular pattern molecules that can initiate and perpetuate immune response; their potential to amplify tissue injury by killing other cells, in addition to their agonistic activity on TLRs, provides a rationale to target histones for therapy. Unfortunately, approaches currently being pursued in experimental models have marked limitations. First, while TLRs clearly mediate the immune response induced by histones, they have no role in calcium-mediated cytotoxicity, negating the use of TLR2/4 neutralizing antibodies. Second, several other biologics that demonstrated efficacy in animal models have failed to provide a therapeutic benefit in clinical trials (activated protein C) or have increased risk of bleeding (heparin, APC) or toxicity (histone deacetylase inhibitors). In addition, many biologics require special handling and storage, special dosing considerations, and risk allergic reactions (e.g., recombinant proteins and antibodies). Given the limitations of current approaches, the development of selective inhibitors of histone-mediated injury is a unique clinical opportunity to interrupt a pathophysiologic cascade responsible for significant morbidity and mortality.

The ideal binding partner of a histone (cationic protein) is an oligonucleotide (anionic molecule). Histones normally associate with DNA in the nucleosome. Given their strong negative charge, oligonucleotides (e.g. RNA aptamers) have extraordinarily high affinity and specificity for positively charged histones, making them the preferred reagent for binding and neutralizing circulating histones. No one has previously attempted to use oligonucleotides to inhibit extracellular histones. RNA aptamers are single-stranded nucleic acids whose binding properties depend on their sequence and structure.

Development and In Vitro Characterization of RNA Aptamers that Selectively Bind to Human Histones.

SELEX is used to identify RNA aptamers with high affinity to human H3 and H4. Studies characterize individual aptamer sequences and define their binding affinity and specificity. (Tuerk C, Gold L. Systematic evolution of ligands by exponential enrichment: RNA ligands to bacteriophage t4 DNA polymerase. *Science,* 1990249:505-510). Studies also use cultured human pulmonary endothelial cells, alveolar epithelial cells, and platelets to confirm the efficacy of RNA aptamers at neutralizing histone-mediated cellular effects.

A. Development of RNA Aptamers to Human Histones H3 and H4.

These studies identify RNA aptamers that selectively bind with high affinity to both human histones H3/H4. Briefly, RNA aptamers with specificity for human H3 and H4 were enriched by pre-clearing a chemically modified RNA aptamer library against control proteins (BSA and human IgG) abundant in serum. Those RNAs that did not bind serum proteins were collected and incubated with either human H3 or H4. Histone-bound RNAs were collected and processed for the next round of selection. Several rounds of selection were performed to enrich for high affinity binders. High affinity aptamers were enriched by modifying the selection conditions at each round of selection (e.g. increasing the RNA:histone ratio during the positive selection step and reducing the incubation time of aptamers with histones H3/H4).

Figure 3A:
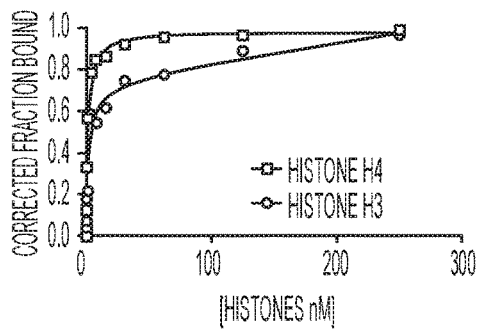
FIGS. 3A-3B. Binding of RNA aptamers to histone H3 and H4 proteins. (A) Binding affinities of H3/H4 to unselected RNA aptamer library as determined by a dot blot filter binding assay. H3 KD=2.1 nM; H4 $K_D$=1.5 nM. (B) Binding affinities of histone H3 to unselected RNA aptamer library (R0) and selected RNA aptamer pools from rounds 2, 4, 6, and 7 of selection were determined as in part A. A leftward shift in binding is indicative of enrichment for higher affinity aptamers. $K_D$ for rounds 6 (RD6) and 7 (RD7)=~0.3 nM.
Figure 3B:
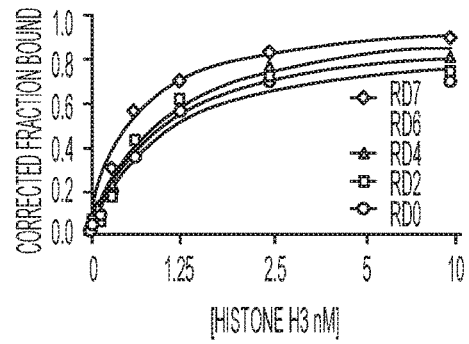

It has been confirmed that the starting, unenriched RNA aptamer library (round 0) binds to the histone proteins with low nM affinity (FIG. 3A). Following seven rounds of selection RNA sequences were enriched with overall higher affinity (high pM range) for the intended histone target (FIG. 3B) (data shown for H3 selection). Finally, round 7 from each selection did not bind to proteins normally found in serum (data not shown), confirming the specificity of the selected RNAs. After 8-10 rounds of selection, final post-selection, enriched aptamer pool has affinities in the low pM range. The progress of the selections are assessed by determining the sequence diversity of the random regions from round to round by high-throughput sequencing (HTS) and identifying sequence and structure families using bioinformatics analyses. Progress of the selections is assessed by carrying out standard in vitro binding assays with the pools of RNA from each round.

B. In Vitro Characterization of Individual RNA Aptamers.

Individual RNA aptamers identified from the sequence analysis are screened for (1) specificity of binding and for (2) ability to inhibit historic activity. In vitro filter binding assays are performed with the top 10-15 sequences from the FITS and bioinformatics analysis as previously described. (Thiel K W, Hernandez L I, Dassie J P, Thiel W H, Liu X, Stockdale K R, Rothman A M, Hernandez F J, McNamara J O, 2nd, Giangrande P H. Delivery of chemo-sensitizing siRNAs to her2+-breast cancer cells using RNA aptamers, *Nucleic Acids Res.* 2012; 40; 6319-6337; Thiel W H, Bair T, Peek A S, Liu X, Dassie J, Stockdale K R, Behlke M A, Miller F J, Jr., Giangrande P H. Rapid identification of cell-specific, internalizing RNA aptamers with bioinformatics analyses of a cell-based aptamer selection. *PLoS One,* 2012; 7:e43836; Thiel W H, Bair T, Wyatt Thiel K, Dassie J P, Rockey W M, Howell C A, Liu X Y, Dupuy A J, Huang L, Owczarzy R, Behlke M A, McNamara J O, Giangrande P H. Nucleotide bias observed with a short SELEX RNA aptamer library. *Nucleic Acid Ther.* 2011; 21:253-263). A more extensive quantitative determination of binding affinities via surface plasmon resonance (SPR) is performed for the 5 aptamers that demonstrate the greatest affinity and specific binding in the filter binding assays (Thiel K W, Hernandez L I, Massie J P, Thiel W H, Liu X, Stockdale K R, Rothman A M, Hernandez F J, McNamara J O, 2nd. Giangrande P H. Delivery of chemo-sensitizing siRNAs to her2+-breast cancer cells using RNA aptamers. *Nucleic Acids Res.* 2012; 40:6319-6337; Huang Y Z, Hernandez F J, Gu B, Stockdale K R, Nanapaneni K. Scheetz T E, Behlke M A, Peek A S, Bair T, Giangrande P H, McNamara J O, 2nd. RNA aptamer-based functional ligands of the neurotrophin receptor, trkb. *Mol Pharmacol.* 2012; 82:623-635; Hernandez L I, Flenker K S, Hernandez F J, Klingelhutz A J, McNamara J O, 2nd, Giangrande P H. Methods for evaluating cell-specific, cell-internalizing RNA aptamers. *Pharmaceuticals (Basel).* 2013; 6:295-319). The best two candidate aptamers that selectively bind H3/H4 in the low pM-low nM range are used to test efficacy in cells in culture. Mutated aptamers that have weak-to-no affinity for histones serve as negative controls. Cells also receive aptamers without histones as a control. To model circulating histone content, human, pulmonary microvascular endothelial cells (EC), human alveolar epithelial cells, or human platelets are exposed to histones purified from calf thymus[5, 7] (contains a heterogeneous mixture of core histones) (Abrams S T, Zhang N, Manson J, Liu T, Dart C, Baluwa F, Wang S S, Brohi K, Kipar A, Yu W. Circulating histones are mediators of trauma-associated lung injury. *American journal of respiratory and critical care medicine.* 2013; 187:160-169; Semeraro F, Ammollo C T, Morrissey J H, Dale G L, Friese P, Esmon N L, Esmon C T. Extracellular histones promote thrombin generation through platelet-dependent mechanisms: Involvement of platelet tlr2 and tlr4. *Blood,* 2011; 118:1952-1961) in the presence or absence of aptamer. Human patient serum with histone levels in excess of 50 µg/ml is toxic to EC (Abrams S T, Zhang N, Manson J, Liu T, Dart C, Baluwa F, Wang S S, Brohi K, Kipar A, Yu W. Circulating histones are mediators of trauma-associated lung injury. *American journal of respiratory and critical care medicine.* 2013; 187:160-169; Xu J, Zhang X, Pelayo R, Monestier M, Ammollo C T, Semeraro F, Taylor F B, Esmon N L, Lupu F, Esmon C T. Extracellular histories are major mediators of death in sepsis. *Nature medicine,* 2009; 15:1318-1321)); therefore this concentration is used in vitro. Dose response curves for the aptamers are determined in vitro and will define the concentration used in in vivo studies. Studies also explore timing of aptamer delivery, in particular if treatment after exposure to circulating histones can prevent cellular toxicity. Cellular toxicity is determined by performing the following measurements: (1) Measurement of calcium influx: Intracellular calcium concentration, will be measured using established protocols with fura 2-AM as the fluorescent probe. (2) Measurement of TLR activation: Expression of IFN-γ, IL-1β, IL-6, and TNF-α will be assessed by PCR. (3) Detection of cell toxicity: Live, apoptotic, and dead cells are determined by flow cytometry following staining with annexin-V and propidium iodide (PI). (4) Measurement of transcellular resistance: Transendothelial and transepithelial electrical resistance is measured across a confluent monolayer using an electrical cell-substrate impedance sensing system.

Figure 4A:
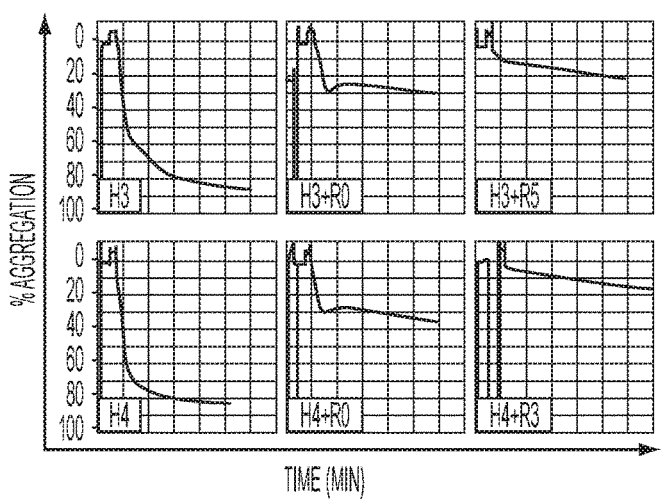
FIGS. 4A and 4B. RNA aptamers inhibit histone-mediated platelet aggregation. Platelet aggregation was performed with washed human platelets and quantitated using an aggregometer at 2 min intervals. (A) Histones H3 (50 mg/mL—top row) and H4 (10 mg/mL—bottom row) induce platelet aggregation. Addition of the unselected round 0 (R0) aptamer pool (10 nM) reduces platelet aggregation. A more pronounced inhibition of platelet aggregation is observed with selected RNA pools (R5 for H3 and R3 for H4). (B) RNA aptamers have no effect on collagen-mediated platelet aggregation (top panels). As a positive control, heparin (1 U/mL) reverses histone-mediated platelet aggregation (data shown for histone H4).
Figure 4B:
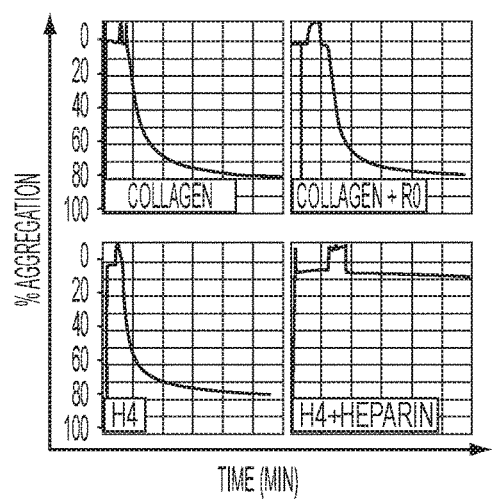

Platelet aggregation: The release of histones from dying cells is associated with microvascular thrombosis. Histone H3 and H4 have been found to be responsible for directly inducing aggregation of human platelets. As an independent measure of aptamer inhibition of histone activity, the effect of individual histone, aptamers is evaluate on historic-mediate platelet aggregation. (Xu J, Zhang X, Pelayo R, Monestier M, Ammollo C T, Semeraro F, Taylor F B, Esmon N L, Lupu F, Esmon C T. Extracellular histories are major mediators of death in sepsis. *Nature medicine,* 2009;

15:1318-1321). It has been shown that histones H3/H4 induce pronounced platelet aggregation which can be inhibited with addition of RNA aptamers (FIG. 4A). Importantly, aptamer inhibition of histone-mediated aggregation was more pronounced with selected aptamer pools (R5 pool for H3; R3 pool for H4) compared to the unselected RNA pool (R0). As a measure of specificity, the RNA aptamers did not reverse collagen-mediated platelet aggregation (FIG. 4B). For these studies, blood is collected from human volunteers, platelet-rich plasma prepared, and platelets isolated. Using the histone and aptamer treatment protocol described above, studies are performed in a collagen-coated flow chamber perfused with washed human platelets as previously described. (Xu J, Zhang X, Pelayo R, Monestier M, Ammollo C T, Semeraro F, Taylor F B, Esmon N L, Lupu F, Esmon C T. Extracellular histones are major mediators of death in sepsis. *Nature medicine,* 2009; 15:1318-1321). In separate studies, platelet surface marker expression (activated α2bβ3 and P-selectin) are detected by fluorescent antibodies followed by flow cytometry.

Evaluate Efficacy and Safety of Histone-Specific RNA Aptamers In Vivo.

The efficacy of the histone specific aptamers in mouse models of MODS/ARDS, TRALI, and smoke inhalation is evaluated. Safety is evaluated in immune-competent mice and human peripheral blood mononuclear cells (PBMCs). Finally, efficacy in humans is evaluated by obtaining serum from critically ill patients and test the ability of aptamers to neutralize histone-mediated toxicity.

A. Animal Models of Disease:

These studies test the efficiency of the histone RNA aptamers in three independent mouse models of histone-induced lung injury (MODS/ARDS TRALI, inhalation lung injury). (Abrams S T, Zhang N, Manson J, Liu T, Dart C, Baluwa F, Wang S S, Brohi K, Kipar A, Yu W. Circulating histones are mediators of trauma-associated lung injury. *American journal of respiratory and critical care medicine.* 2013; 187:160-169; Ward P A, Grailer J J. Lung inflammation and damage induced by extracellular histones. *Inflammation and Cell Signaling,* 2014; 1; Chen R, Kang R, Fan X G, Tang D. Release and activity of histone in diseases. *Cell Death Dis.* 2014; 5:e1370). For each protocol, a control aptamer (mutant aptamer that has low-to-no affinity for histones) is administered and the H3 and H4-specific aptamers (one for each histone) is identified with the in vitro functional experiments as most effective at neutralizing histone-mediated toxicity. Aptamers are tested at different doses and administered at various times after the "injury". Animals are pretreated with the aptamers (0.1 mg/kg or 1 mg/kg, IV) at various times related to the injury to test the ability to prevent development or abort progression of tissue injury. The doses are adjusted as indicated based on the binding data to identify the lowest effective dose. In separate experiments, the aptamer is administered at various times after delivery of the histones (5, 15, and 30 minutes) to examine the ability of the aptamer to prevent injury after the presence of circulating histones. Noninvasive determination of respiratory function (reduced $O_2$ saturation) is continuously monitored using a pulse oximeter. After 3 h (or at the time of death if occurs prior to 3 h) the mice are sacrificed and the following performed: (1) Alveolar permeability and inflammation; Tracheas are isolated and cannulated and the lungs flushed with sterile PBS. Cytospins of BALF cells are stained with modified Wright-Giemsa. Alveolar permeability is assessed by quantitative detection of mouse albumin in BALF by ELISA. (2) Lung histology. Lungs are fixed, embedded and sectioned. Sections are stained with hematoxylin and eosin (H&E) and Mallory's phosphotungstic acid-hematoxylin staining for fibrin then examined by a pathologist for evidence of neutrophils in alveolar spaces, capillary congestion, intra-alveolar hemorrhage, fibrin deposits and thrombi. (3) TLR activation. Blood is collected and serum isolated and stored at −80° C. Cytokines/chemokines are all quantified using a customized multiplex magnetic bead panel kit. (4) Platelet FACS. Platelet surface marker expression (activated α2bβ3 and P-selectin) as a measure of platelet activation, are detected by fluorescent antibodies followed by flow cytometry.

Nonspecific Immune Activation:

Thorough studies are performed to evaluate any potential nonspecific immune effect of the histone RNA aptamers. For these studies, doses of the RNAs that are 10-fold greater than those found to be effective in vivo, are injected in the tail veins of C57/BL6 male mice. Blood from treated animals is collected by cardiac puncture at 1 h, 6 h and 12 h after the first administration of the RNA. Collected blood sera is analyzed using the Bio-Rad Bioplex platform to assess the levels of 23 different cytokines (Kaul R, Johnson K, Scholz H, Marr G. Performance of the bioplex 2200 autoimmun vasculitis kit. *Autoimmun Rev.* 2009; 8:224-227). Spleens and livers from treated mice will also are collected at early (0.5 hrs), intermediate (6 hrs), and late (24 hrs) time points following injection of the RNA and processed for total RNA. Levels of inflammatory cytokines, interferons and viral RNA recognition genes are quantified using RT-qPCR as previously described. (Dassie J P, Hernandez L I, Thomas G S, Long M E, Rockey W M, Howell C A, Chen Y, Hernandez F J, Liu X Y, Wilson M E. Targeted inhibition of prostate cancer metastases with an RNA aptamer to prostate-specific membrane antigen. *Molecular Therapy,* 2014). Polyinosinic:polycytidylic acid (Poly I:C) is used as a positive control for immune stimulation. Histological analysis of tissue sections is performed to determine if specific immune cell populations infiltrate specific tissues in response to RNA therapy. (Judge A D, Bola G, Lee A C, MacLachlan I. Design of non-inflammatory synthetic siRNA mediating potent gene silencing in vivo. *Mol Ther.* 2006; 13:494-505).

C. Obtain Serum from Critically Ill Patients and Test Ability of Aptamers to Neutralize Histone-Mediated Toxicity.

Blood samples are collected via initial placement of a 16 g or larger peripheral IV into citrated tubes after admission to the intensive care unit. Following centrifugation, control or histone targeting aptamers are added to the platelet-rich plasma. Platelets are isolated and surface marker expression (activated α2bβ3 and P-selectin) is detected by fluorescent antibodies followed by flow cytometry. The serum is added to cultured microvascular endothelial cells and toxicity measured as described above. Circulating histone levels are measured in the serum using an ELISA assay.

Example 2

Schematic of In Vitro SELEX Technology.

The DNA aptamer library contains a variable region of 20 bases flanked by two constant regions (FIG. 5): 1) The DNA template library is in vitro transcribed into RNA using a modified T7 RNA polymerase enzyme that enables the incorporation of chemically modified NTPs. 2) The RNA library is incubated with an irrelevant protein (control protein) for the preclear step to remove non-specific binders. 3) Those RNA aptamers that do not bind the control protein are then incubated with a target protein. 4) Unbound aptamers are removed and RNA aptamers bound to target protein are recovered, reversed transcribed using RT-PCR, 5) PCR amplified, and 6) in vitro transcribed in the presence of chemically modified NTPs (e.g. 2'-fluoro modified pyrimidines). Several rounds (2-10) are carried out to generate a library of aptamers with high affinity and specificity for the specific target.

Aptamer Inhibitors of Extracellular Histones for the Treatment of Sepsis.

Figure 6:
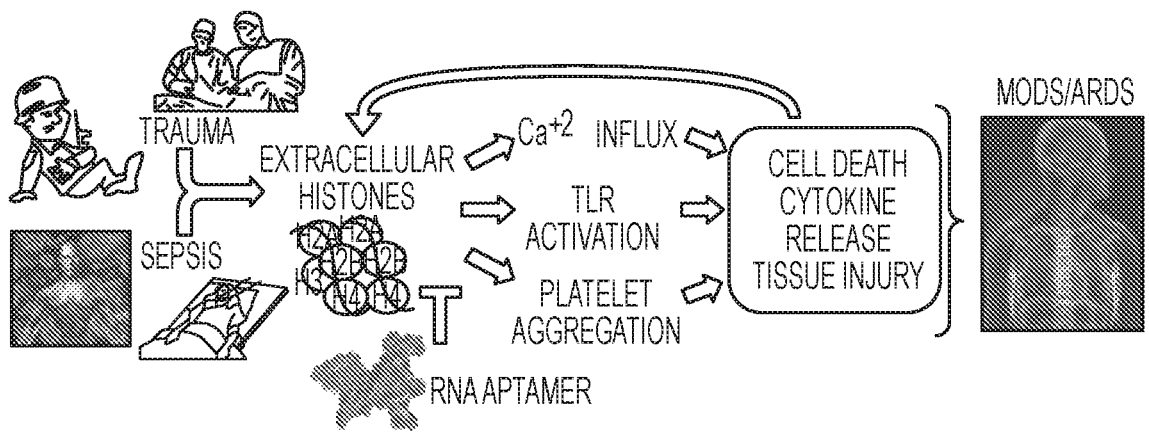
FIG. 6. Aptamer Inhibitors of Extracellular Histones for the Treatment of Critical Illness.

Tissue damage and diseases cause cells to release histones into the circulation (referred to as circulating or extracellular histones) (FIG. 6). The circulating histones go on to propagate release of more histones by the tissue injury and cell death.

Figure 7:
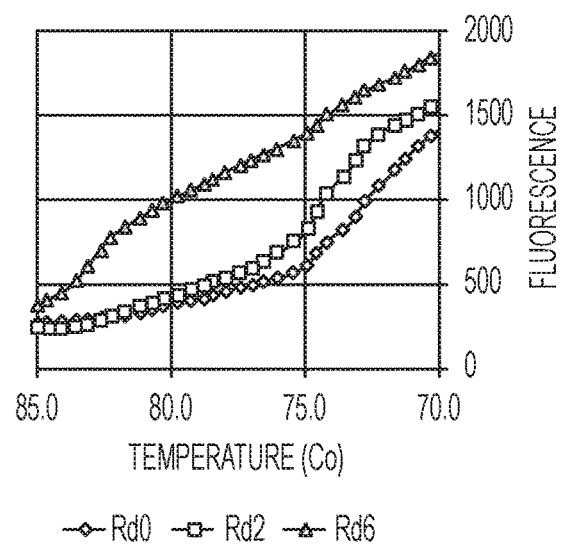
FIG. 7. Complexity assay.

Complexity Assay (FIG. 7).

A complexity assay was performed by mixing 10 µl of 0.5 µM DNA duplex library from selected rounds to 10 µl of SYBR green (BioRad, 170-8882). These samples were run in a 96 well plate on a real-time PCR machine (Eppendorf, Mastercycler epgradient S with realplex$^2$) using the gradient PCR protocol, 95° C. for 15 min; 95° C.-25° C. reducing the temperature every 15 sec.; 4° C. hold). The florescence from the raw data (performed in triplicate) was averaged then plotted as fluorescence intensity (SYBR) vs. temperature (C°). Reduction in complexity was shown by the relative shift of the DNA melt curve towards higher temperatures. DNA from Round 0 and H4 selected rounds 2 and 6 went through a reverse melt curve. Higher library complexity was seen in rounds 0 and 2 by a relative shift of the DNA melt curve towards lower temperatures, whereas, Round 6 shifted to a higher temperature indicating a lower library complexity.

Figure 8A:
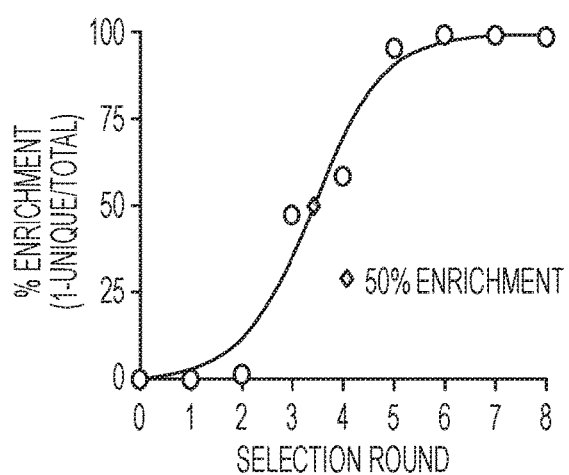
FIGS. 8A-8B. Sequence Enrichment data.
Figure 8B:
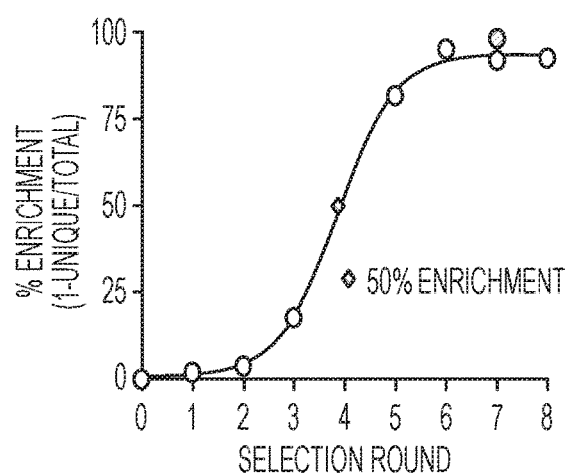

Sequence Enrichment of Aptamers for Histones (FIG. 8).

The sequence enrichment (% Enrichment) was determined for aptamers from the A) H3.2 and B) H4 aptamer selections. Sequence enrichment was determined for each round of selection (Selection Round) from read counts determined from Illumina sequencing using the following equation; % Enrichment-1-(unique sequences/total sequences). Unique sequences refers to the number of different sequences identified within a selection round and total sequences refers to the total number of reads from a selection round including all duplicate reads.

Figure 9A:
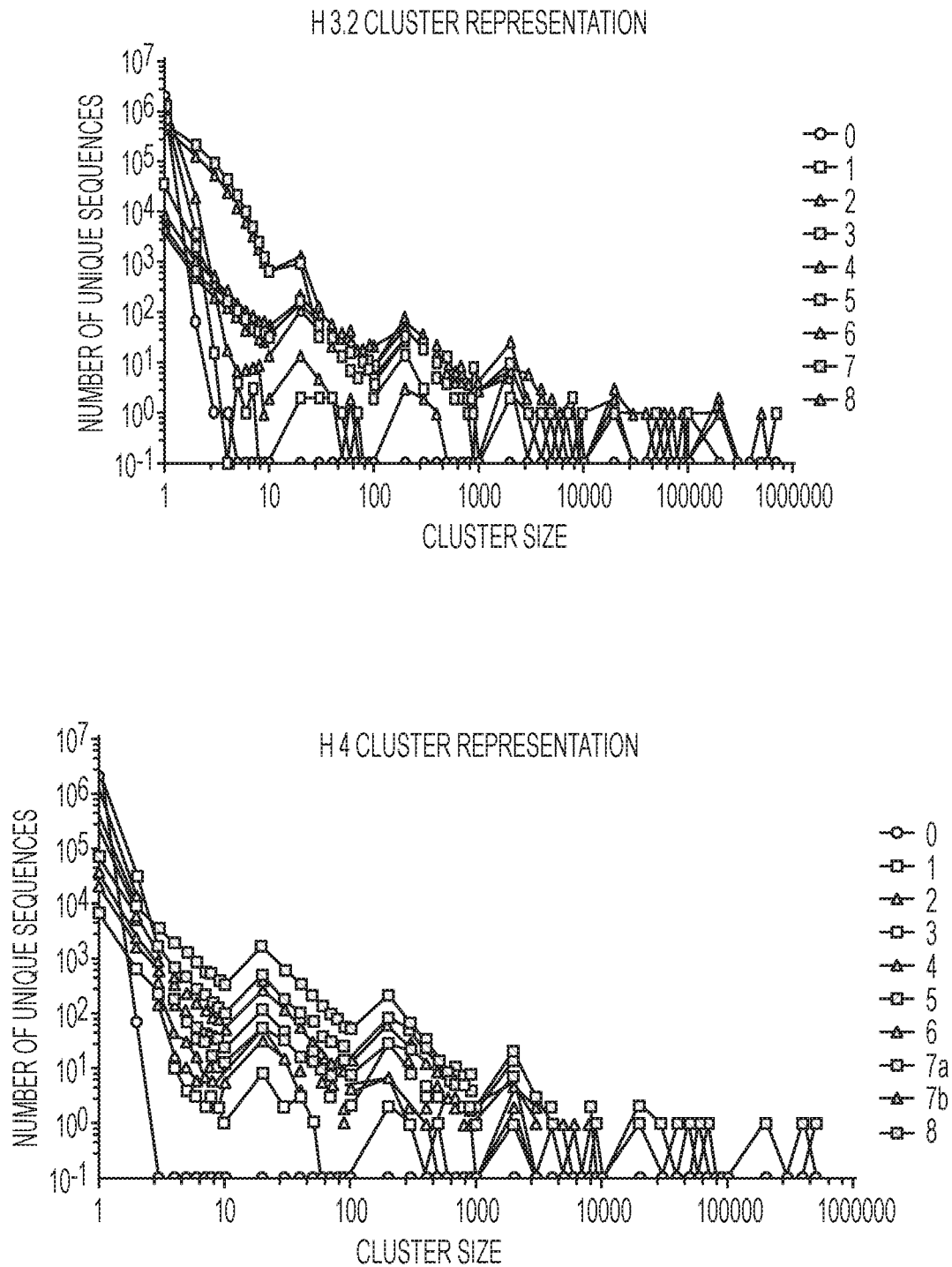

Separation of Non-Selected Aptamer Sequences from Selected Aptamer Sequences (FIGS. 9A-9B).

The A) read counts (Cluster Size) and B) round representation of H3.2 (left panels) and H4 (right panels) selection rounds (1-8) were compared to a pool of non-selected aptamers (round 0) to identify selected aptamers. Selected aptamers exhibit two properties, abundance and persistence. Selected aptamer will accumulate during the selection process (abundance) and the selected aptamers will appear in more than one selection rounds (persistence). The read count (Cluster Size) analysis examines aptamer abundance by plotting the distribution of read counts within each selection round of aptamer (rounds 0-8). The round representation analysis examines aptamer persistence by first determining the number of selection rounds each aptamer sequence was observed and second plotting the distribution of round representation for all aptamers within each selection round. Aptamers with read counts significantly greater than the read counts observed in round 0 (>4 reads) and that appear in at least two selection rounds are classified as selected.

Histone Aptamer Sequences (FIG. 10).

Figure 11:
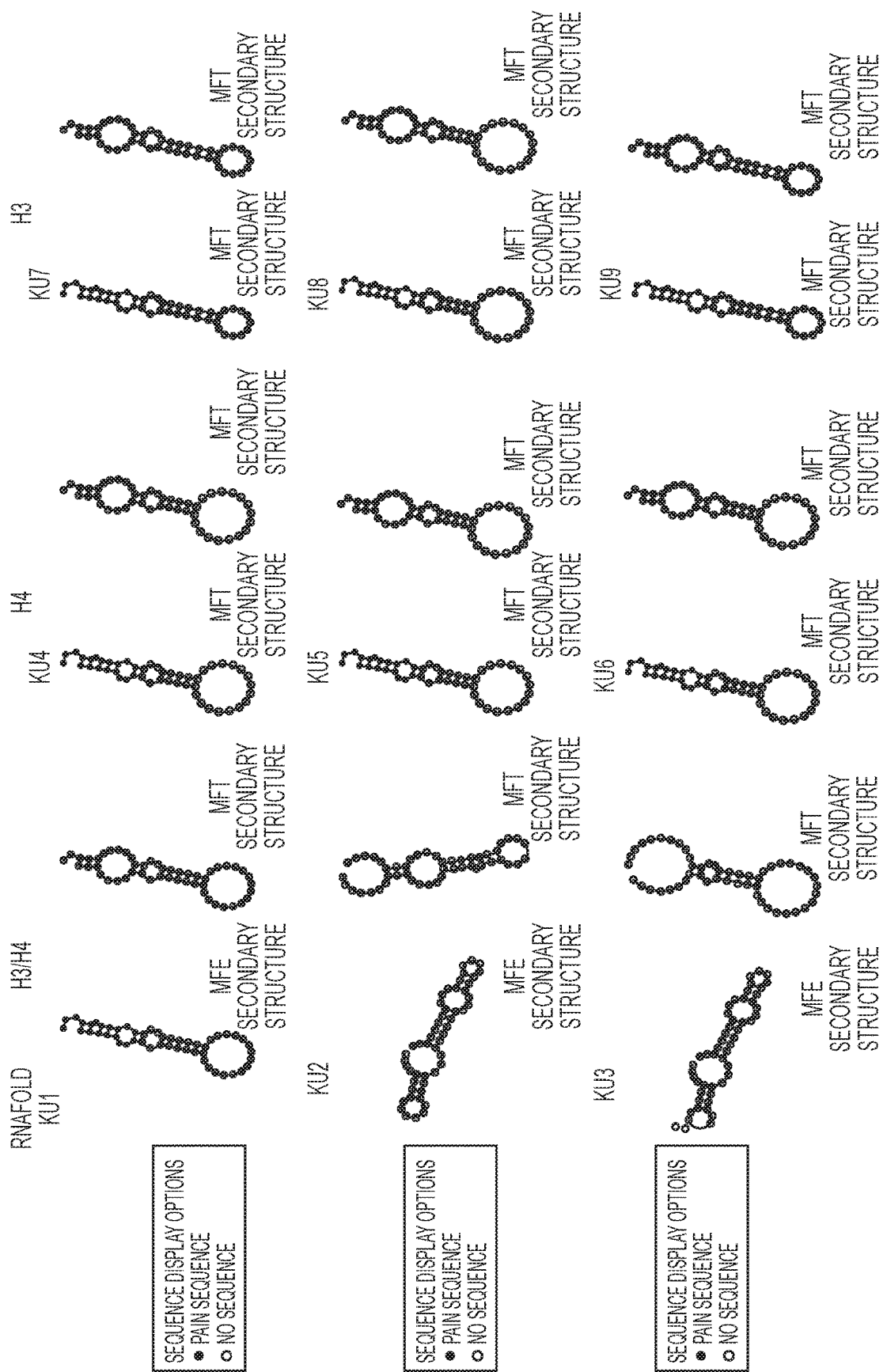
FIG. 11. Predicted secondary structure of selected aptamer sequences. Figure discloses KU1-KU9 structures as SEQ ID NOS 7598, 7619, 7620, 10754, 10749, 10765, 7741, 7832, and 7839, respectively.

These aptamers have read counts significantly greater than the read counts observed in round 0 (>4 reads) and that appear in at least two selection rounds are classified as selected. These nine aptamers had the largest Log 2 fold change between rounds 6:8. They were further selected by their presence in either both or one of the selections. The full list of selected aptamers is in Table 1 below, Predicted Secondary Structure of Selected Aptamer Sequences (FIG. 11).

The sequences from FIG. 10 were imputed into the RNA fold program to generate the possible secondary structures (Website: http://rna.tbi.univie.ac.at/cgi-bin/RNAfold.cgi)

Figure 12:
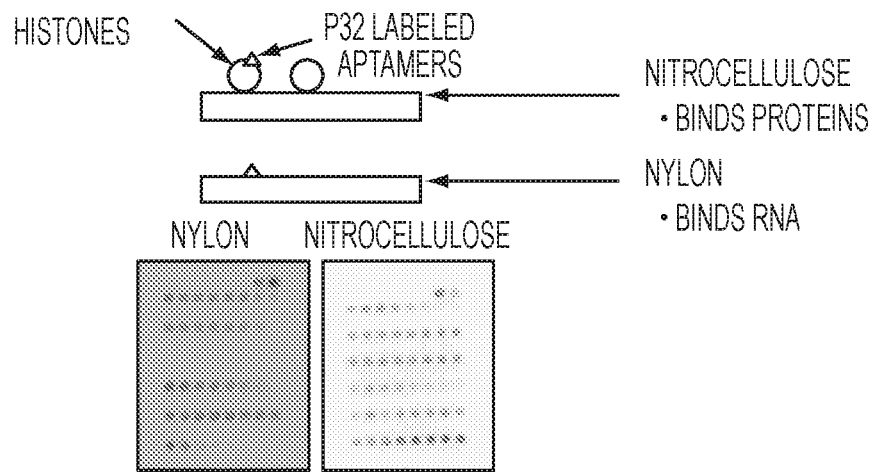
FIG. 12. Double-filter binding assay.

Filter Binding Assay Protocol (FIG. 12).

One hundred pmoles of purified RNA aptamers were dephosphorylated by Bacterial Alkaline Phosphatase (Promega) and were labeled with $^{32}$P-gamma ATP (6,000 Ci/mmol) by T4 PNK (Promega). The radiolabeled aptamers were then purified on G25 columns (GE Healthcare) and counted on a Scintillation Counter. The RNA amount was adjusted to 2,000 CPM/µl and folded by heating at 95° C. for 5 minutes, 65° C. for 5 minutes, and 37° C. for 10 minutes in the selected buffer. Serial dilutions of Histones starting from 250 nM were made in selection buffer. Five microliter of RNA was incubated with 15 µl of protein for 5 minutes at 37° C. filtered through Nitrocellulose (top) and Nylon (bottom) double-filters using dot-blot apparatus (Nalgene, Rochester, N.Y.). CL-X film was exposed by membranes for 30 minutes at RT and was imaged on the typhoon. ImageJ 1.38x software (Wayne Rasband; NIH, Bethesda, Md.) was used to determine relative optical density of radiographed spots in NC-filter binding assay, these data been used to calculate amount of radioactive RNA in each spot. (Wong I, Lohman T M. A double-filter method for nitrocellulose-filter binding: application to protein-nucleic acid interactions. Proc Natl Aad Sci USA 1993; 90: 5428-32.)

Figure 13A:
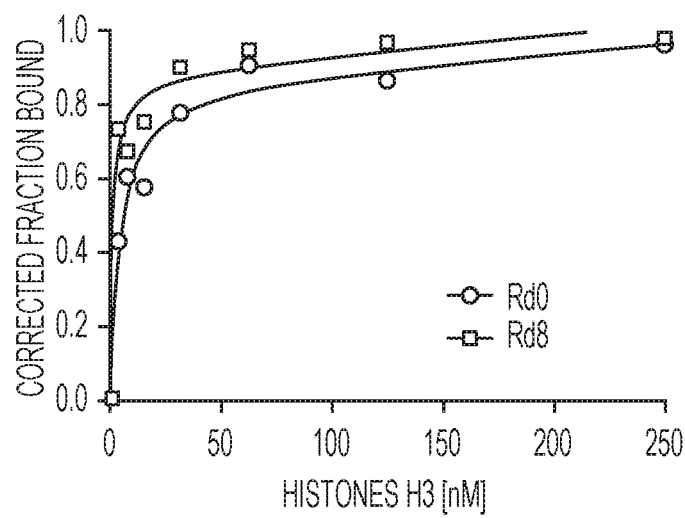
FIGS. 13A-13B. Binding data of rounds 0 and 8 of selection.
Figure 13B:
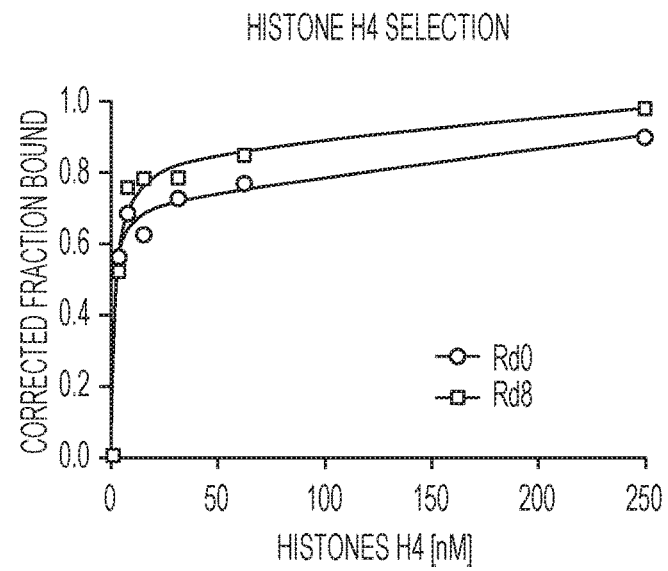

Progression of RNA Aptamer Selection for Histones H3 and H4 Measured by Filter Binding Assay (FIGS. 13A-13B).

Figure 14A:
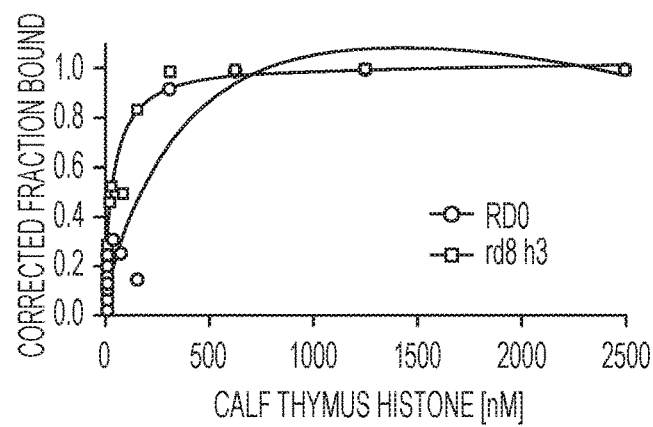
FIGS. 14A-14B. Binding data of rounds 0 and 8 of selection to calf thymus histones.
Figure 14B:
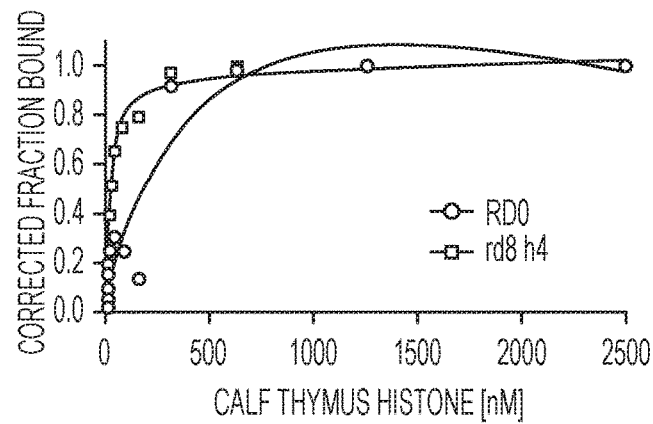

Binding of histone H3.2 (a) and histone H4 (B) to unselected RNA aptamer library (RD0) and selected RNA aptamer pool from round 8 of Selection (RD8). A leftward shift in binding is indicative of enrichment for higher affinity aptamers. H3 RD8 $K_D$=0.6 nM; H4 Rd8 $K_D$0.3 nM Binding Data of Rounds 0 and 8 of Selection to Calf Thymus Histones (FIGS. 14A-14B).

Binding of selected library (round 8-Rd8) and unselected library (RD0) to calf thymus histones was measured by filter binding assay as above. Rd8=squares; RD0=circles. Histone (calf thymus) is a natural mixture of the histones H1, H2A, H2B, H3 and H4. These histones still retain their posttranslational modifications.

Figure 2A:
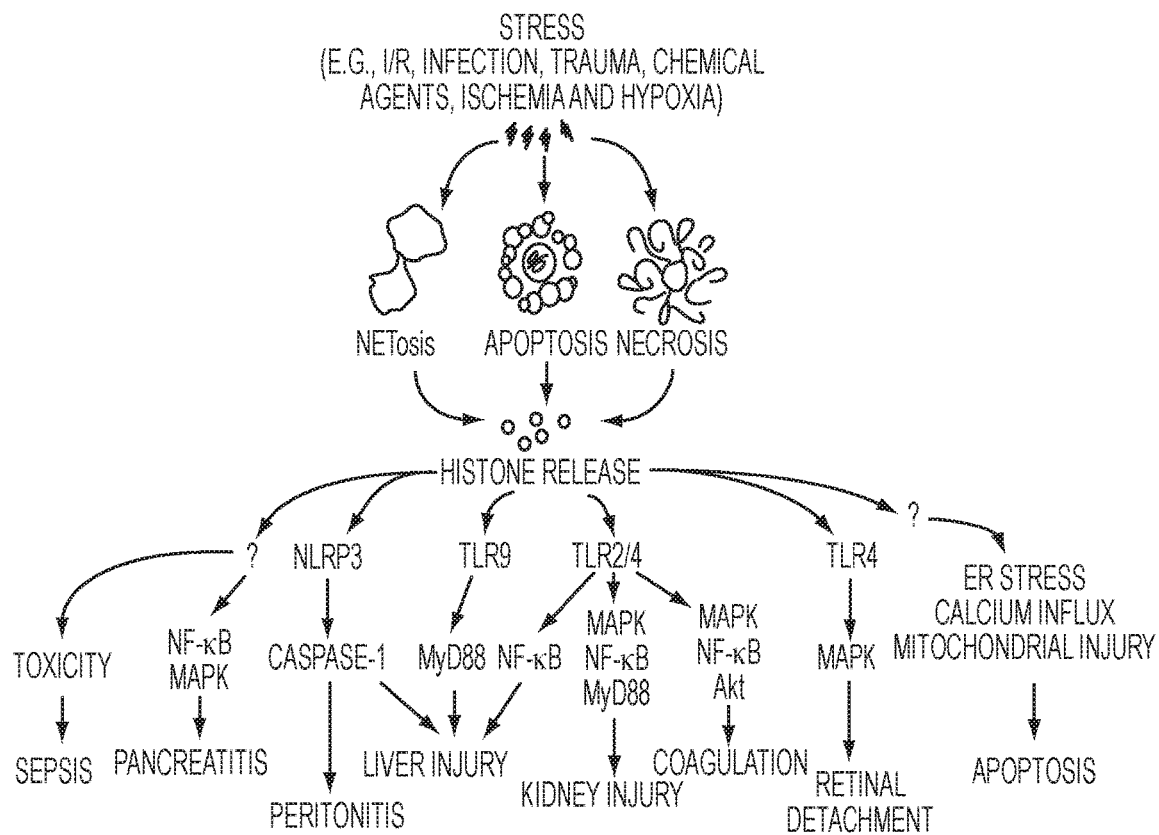
FIGS. 2A-2B. Extracellular histones mediate self-propagating diverse tissue injury.
Figure 2B:
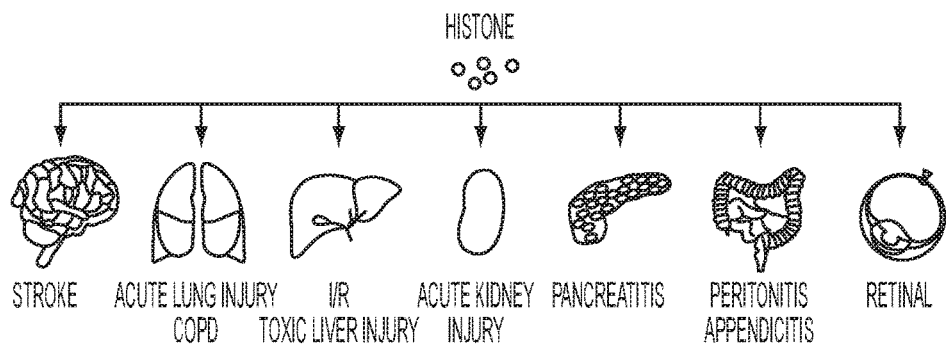
Figure 15A:
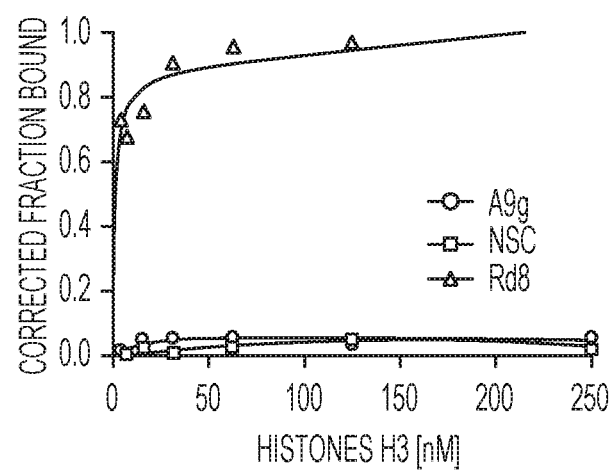
FIGS. 15A-15B. Binding specificity of selected round 8 RNA pool.
Figure 15B:
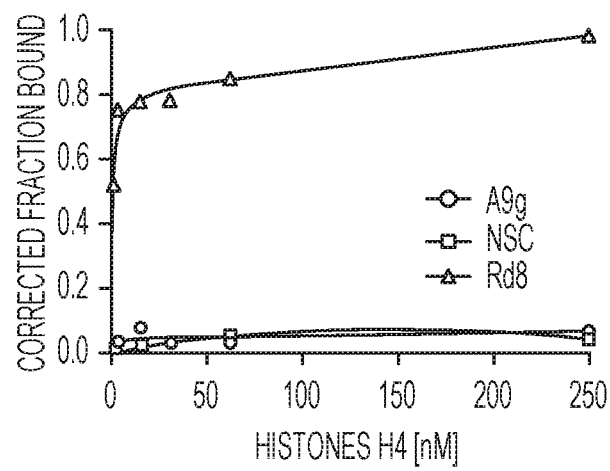
Figure 16A:
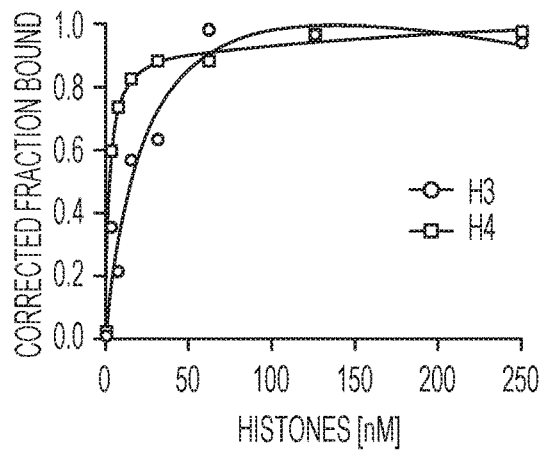
Figure 16B:
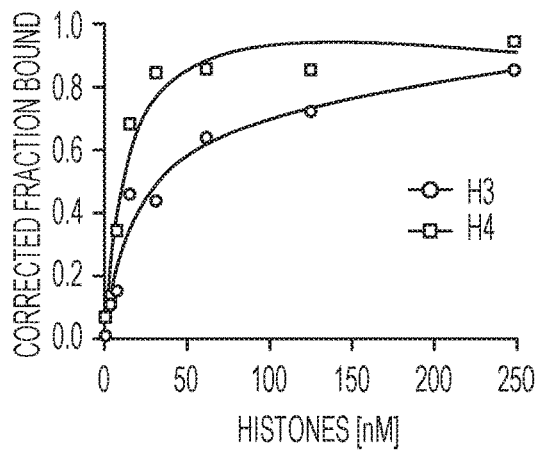
Figure 16C:
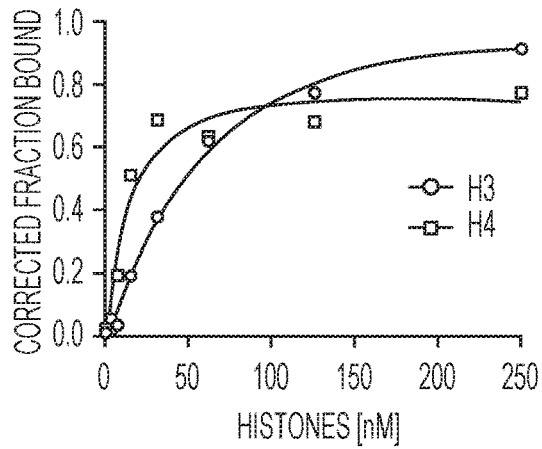
Figure 16D:
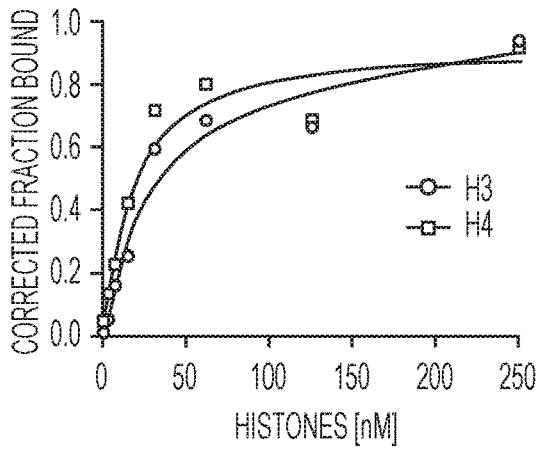
Figure 16E:
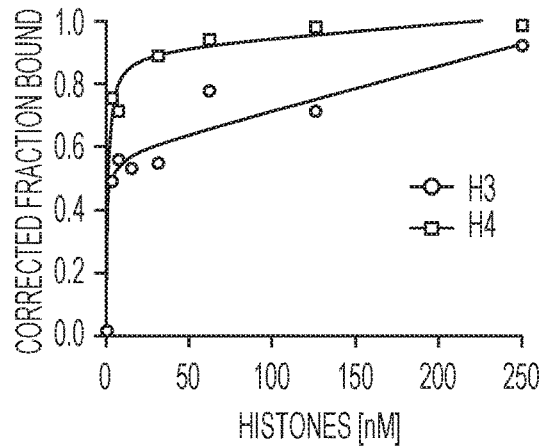
Figure 16F:
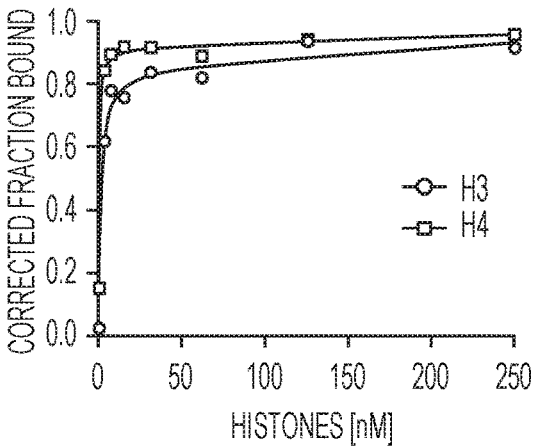
Figure 18A:
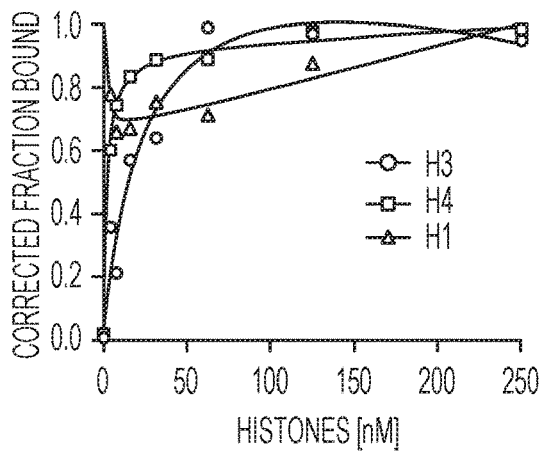
Figure 18B:
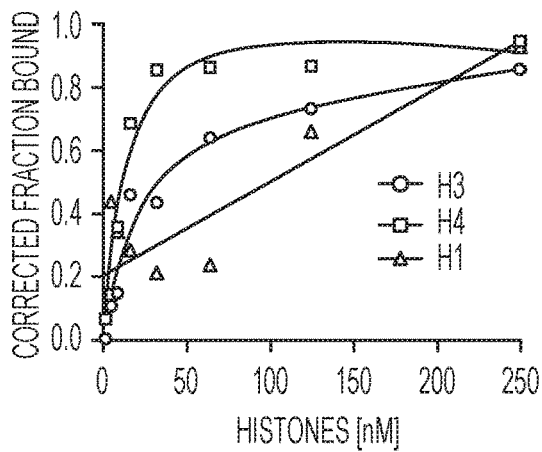
Figure 18C:
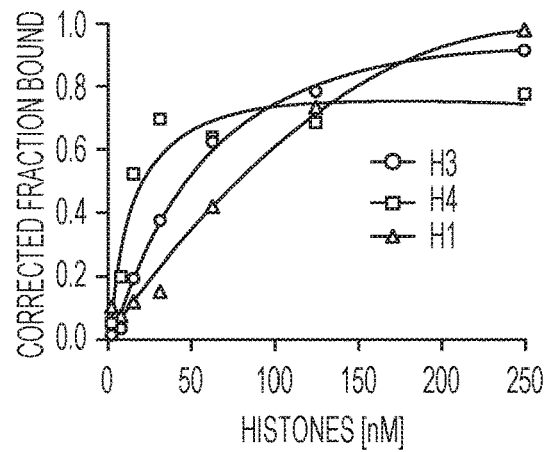
Figure 18D:
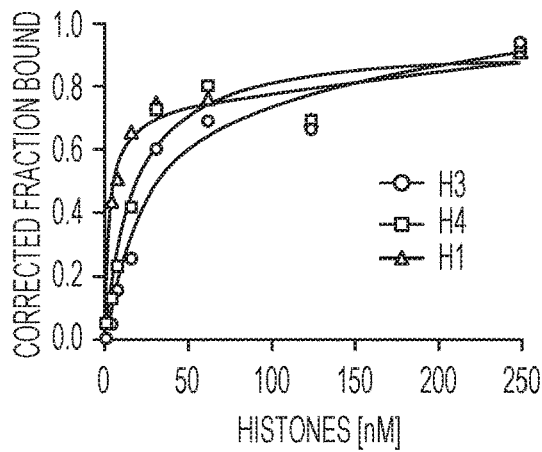
Figure 18E:
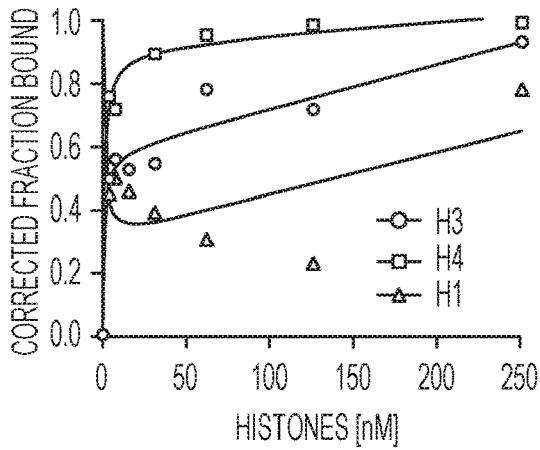
Figure 18F:
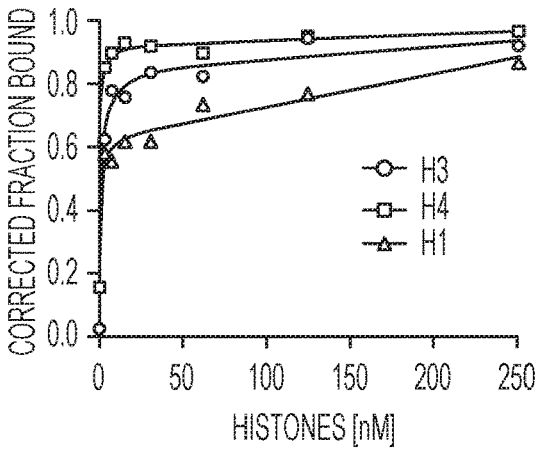
Figure 20A:
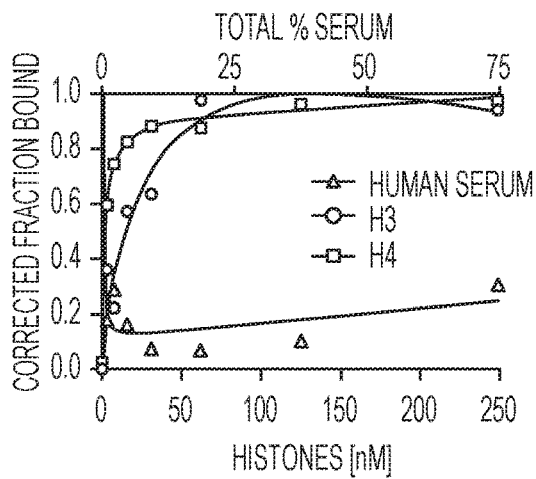
FIGS. 20A-20I. Binding data of individual RNA aptamers to histones H3 and H4, and human serum.
Figure 20B:
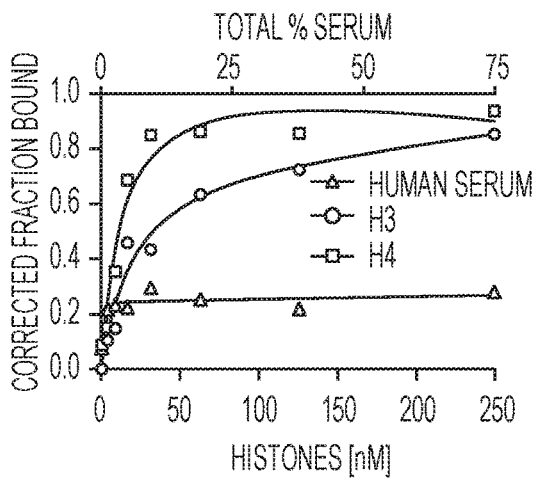
Figure 20C:
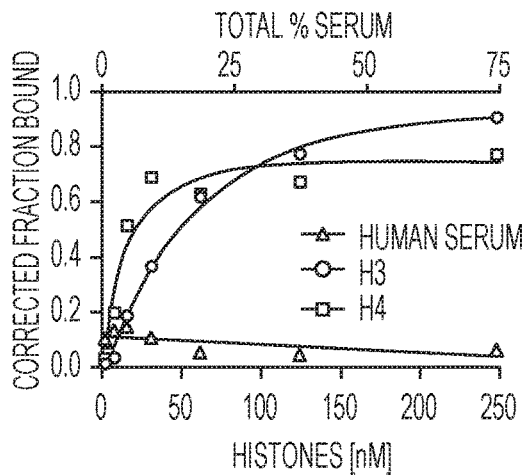
Figure 20D:
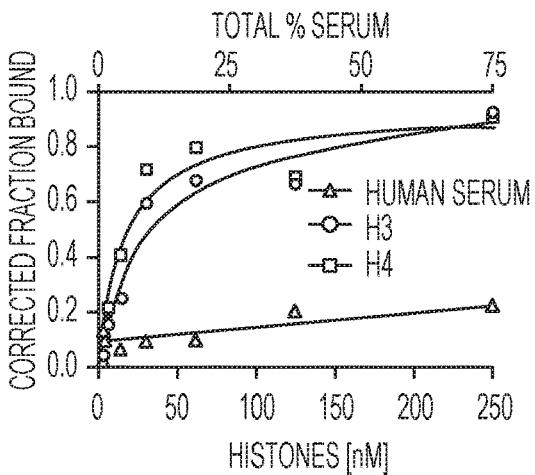
Figure 20E:
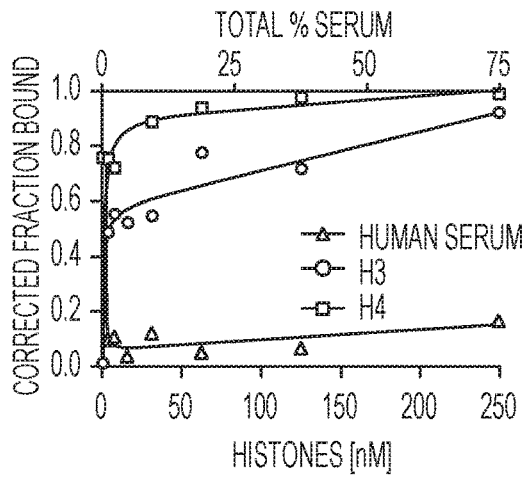
Figure 20F:
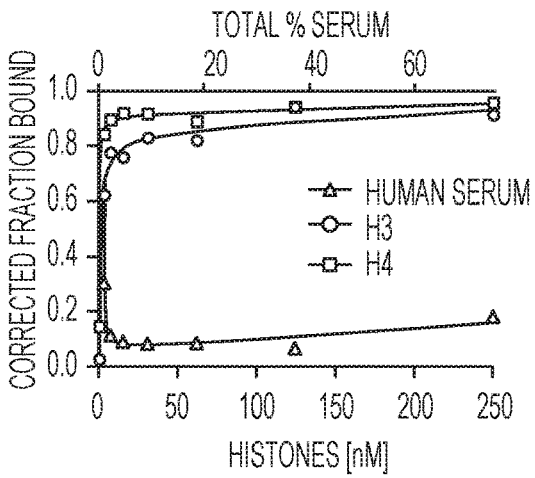
Figure 20G:
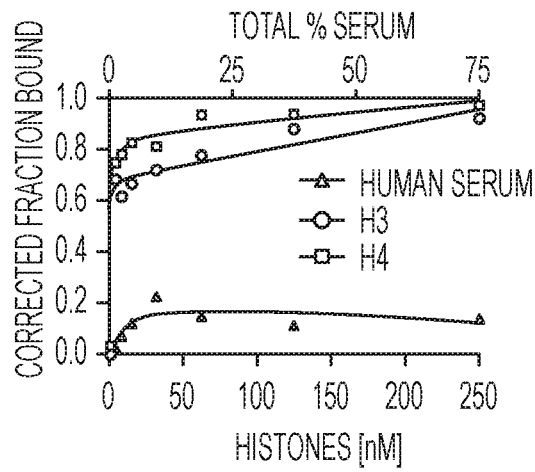
Figure 20H:
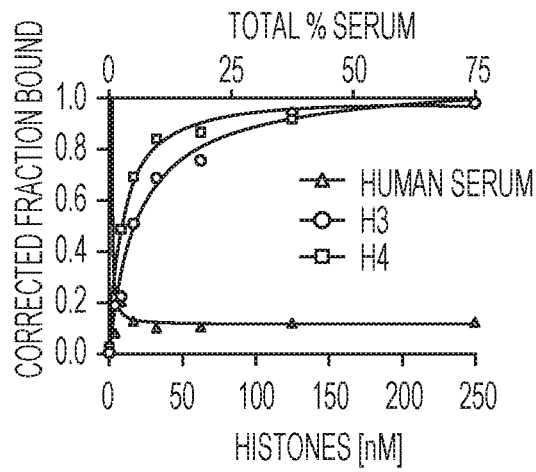
Figure 20I:
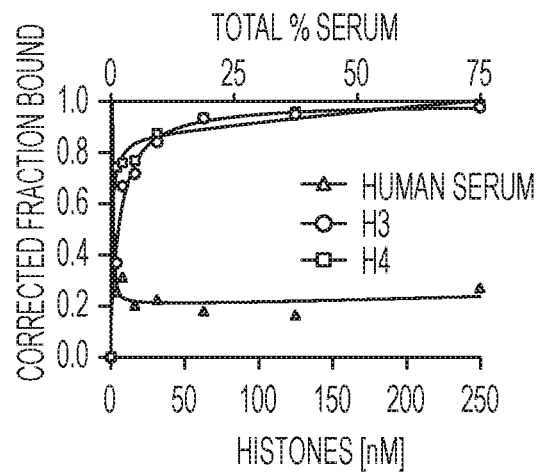

Binding Specificity of RNA Aptamers (FIGS. 15A-15B2).

Binding of selected library (round 8—Rd8) and control RNAs (NSC and A9g) to histones H3 and H4 was measured by filter binding assay as above. Rd8=triangles; NSC=squares; A9g=circles.

Binding of Individual RNA, Aptamers to Histone H3 and H4 Proteins (FIGS. 16A-16I).

Binding of aptamers KU1 (A), KU2 (B), KU3 (C), KU4 (D), KU5 (E), KU6 (F), KU 7 (G), KU 8 (H), KU 9 (1) to histones H3 (light circles) and H4 (dark squares) measured by filter binding assay.

Binding affinities ($K_D$) of the different clones in FIGS. 16A-16I for H4 and H3 (FIG. 17).

Binding of Individual RNA Aptamers to Histone H1, H3, and H4 Proteins (FIGS. 18A-18I).

Binding of aptamers KU1 (A), KU2 (B), KU 3 (C), KU4 (D), KU5 (E), KU6 (F), KU 7 (G), KU 8 (H), KU 9 (I) to histones H1 (triangles), H3 (light circles), and H4 (dark squares) measured by filter binding assay.

Binding Affinities ($K_D$) of the Different Clones in FIG. 4 for H1, H3 and H4 (FIG. 19).

Binding of individual RNA aptamers to histone H3, H4, and Human Serum (FIGS. 20A-20I).

Binding of aptamers KU1 (A), KU2 (B), KU 3 (C), KU4 (D), KU5 (E), KU6 (F), KU 7 (U), KU 8 (H), KU 9 (I) to Human Serum (triangles). H3 (light circles), and H4 (dark squares) measured by filter binding assay.

Figure 5:
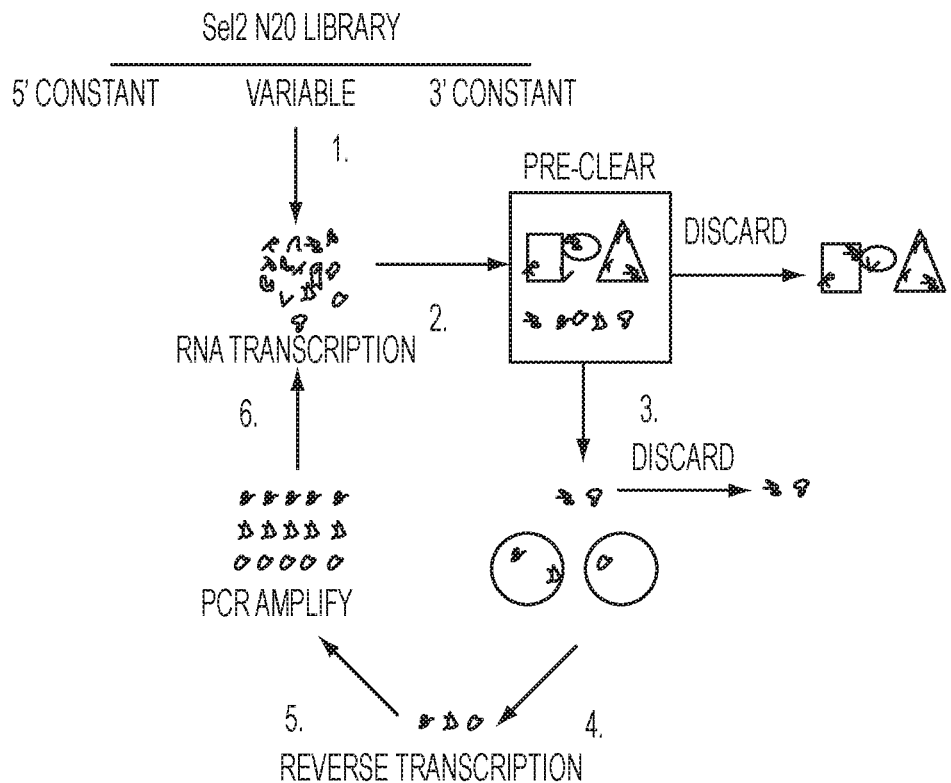
FIG. 5. Schematic of in vitro SELEX technology.

Binding Affinities ($K_D$) of the Different Clones in FIG. 5 for Histones H3, H4, and Human Serum (FIG. 21).

Binding of Individual RNA Aptamers to Histone H3, H4, and Human Albumin (FIGS. 22A-22I).

Binding of aptamers KU1 (A), KU2 (B), KU 3 (C), KU4 (D), KU5 (E), KU6 (F), KU 7 (G), KU 8 (H), KU 9 (I) to Human Albumin (triangles), H3 (light circles), and H4 (dark squares) measured by filter binding assay.

Figure 22C:
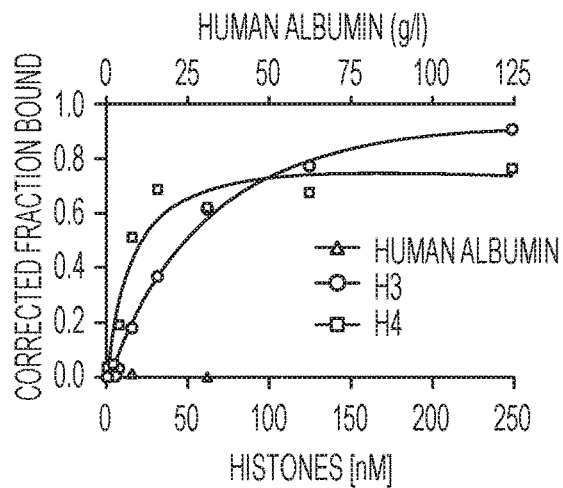
Figure 22D:
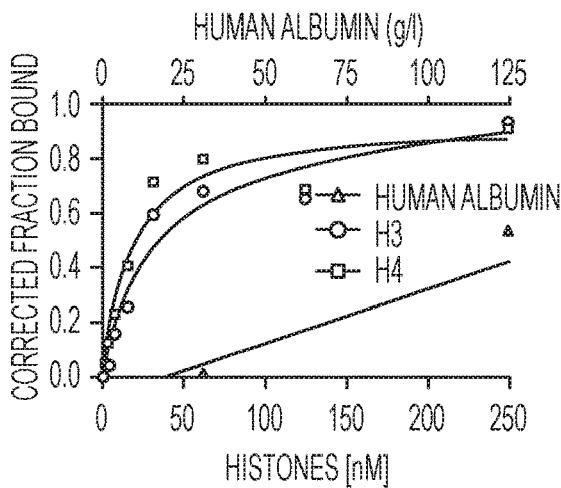
Figure 22E:
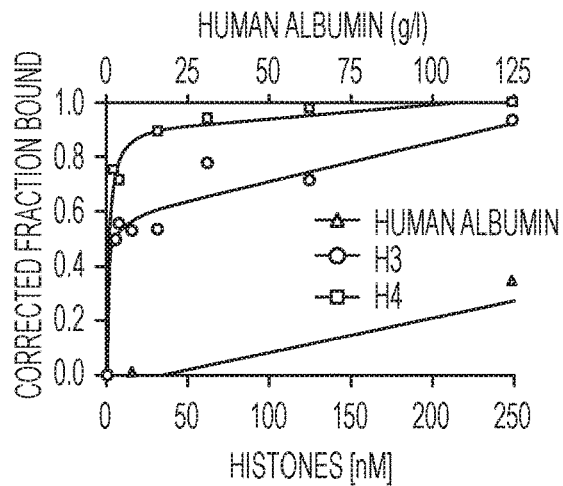
Figure 22F:
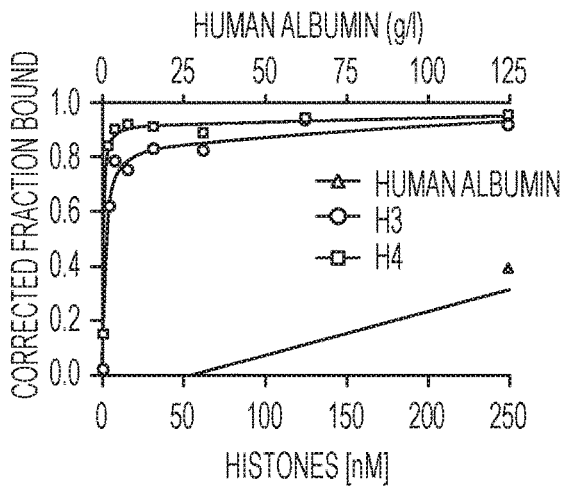
Figure 22G:
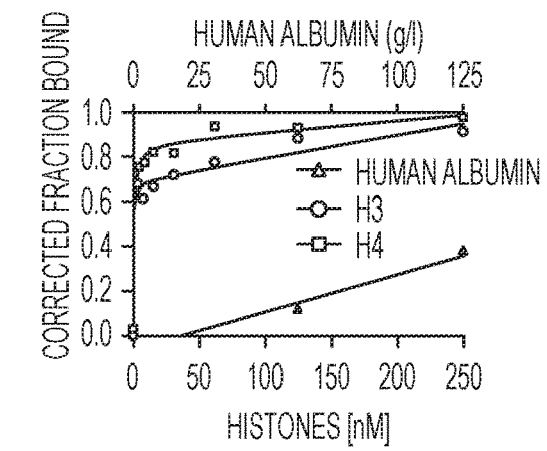
Figure 22H:
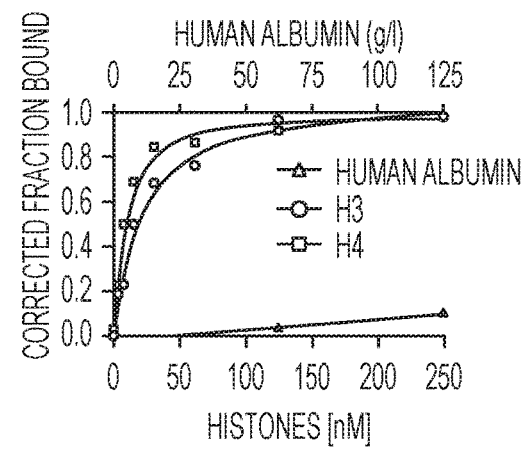
Figures 22I, 23:
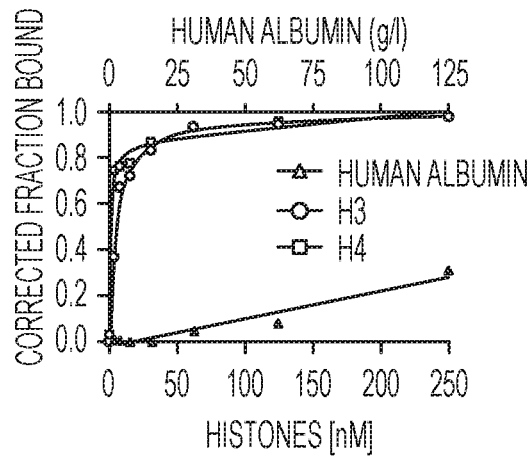

Binding Affinities ($K_D$) of the Different Clones in FIG. 6 for Histones H3, H4, and Human Albumin (FIG. 23).

Figure 24A:
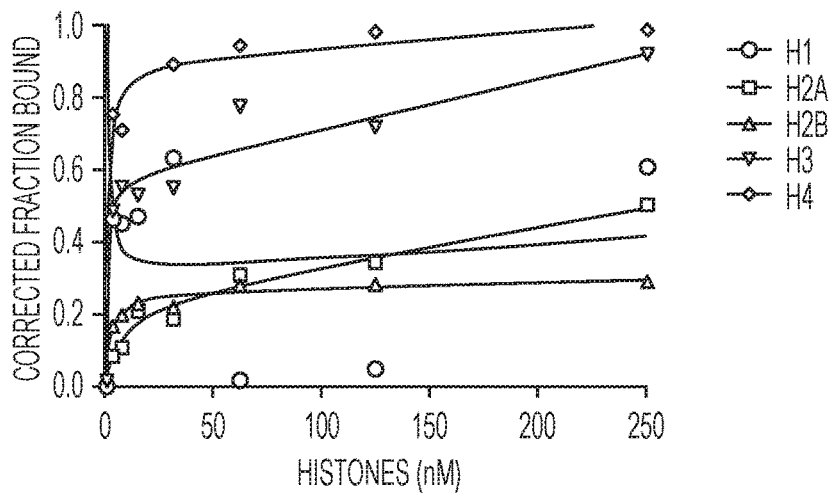
FIGS. 24A-24C. Binding data of individual RNA aptamers to histones H1, H2A, H2B, H3 and H4 proteins.
Figure 24B:
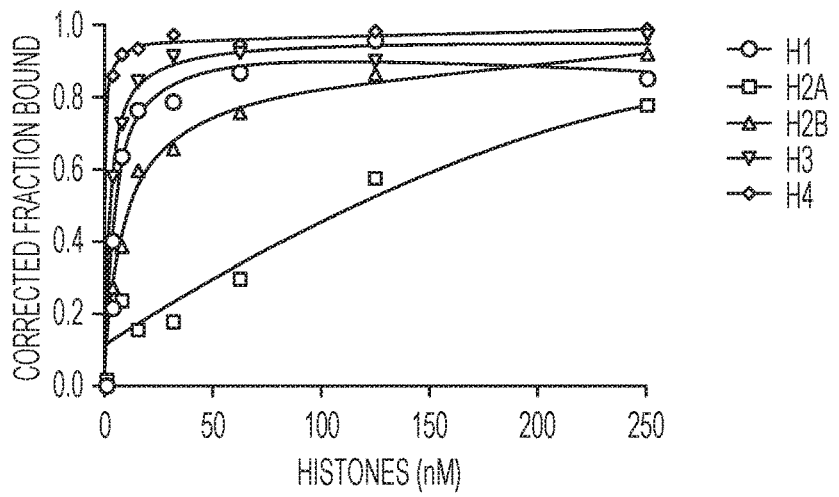
Figure 24C:
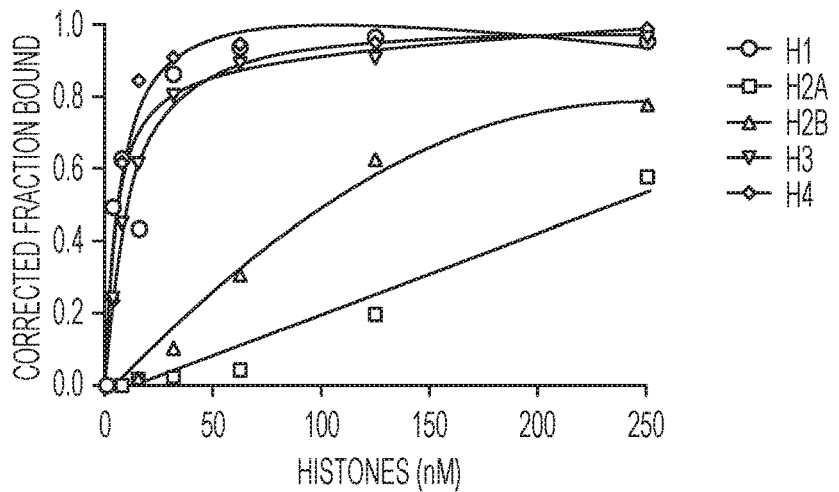

Binding of Individual RNA Aptamers to Histone H1, H2A, H2B, H3, and H4 Proteins (FIGS. 24A-24C).

Binding of aptamer clones (A) KU5, (B) KU7, (C) KU9 to histones H1 (circles), H2A (squares), H2B (upward triangle), H3 (downward triangle), and H4 (diamonds) measured by filter binding assay.

Figures 25, 26:
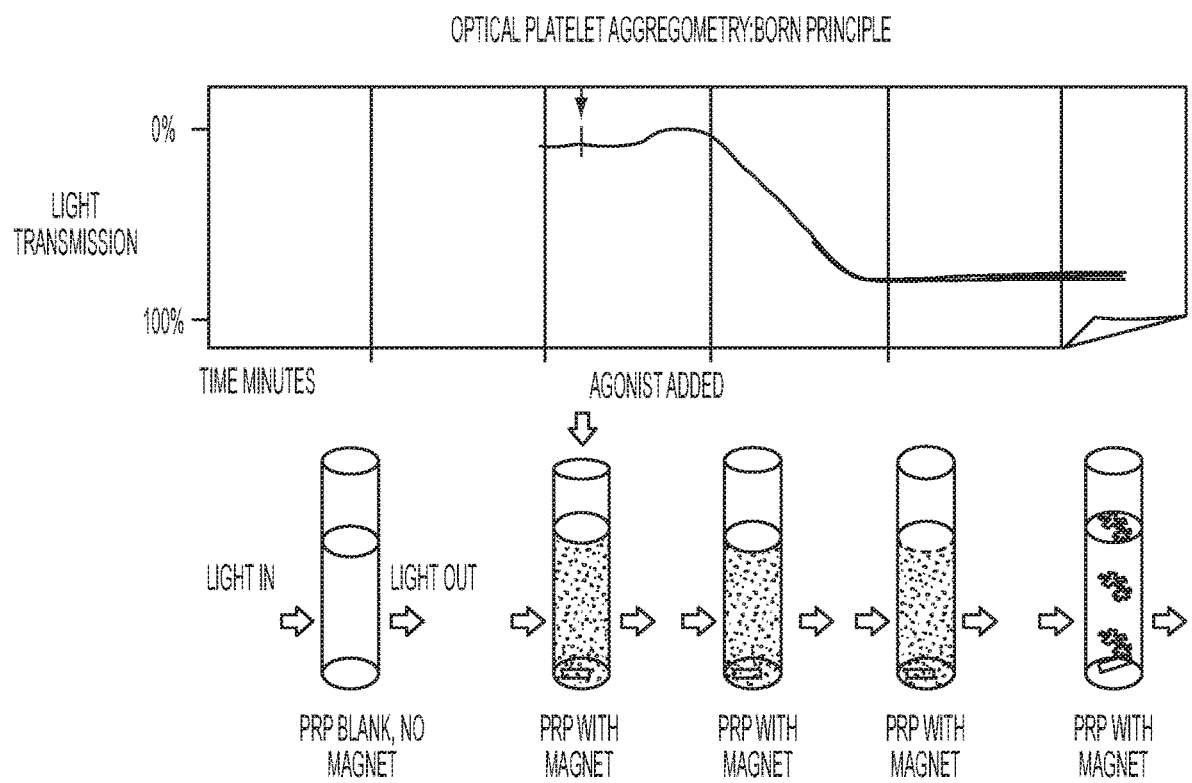
FIG. 25. Table of binding affinities.
FIG. 26. Schematic of platelet aggregometer.
Figure 27A:
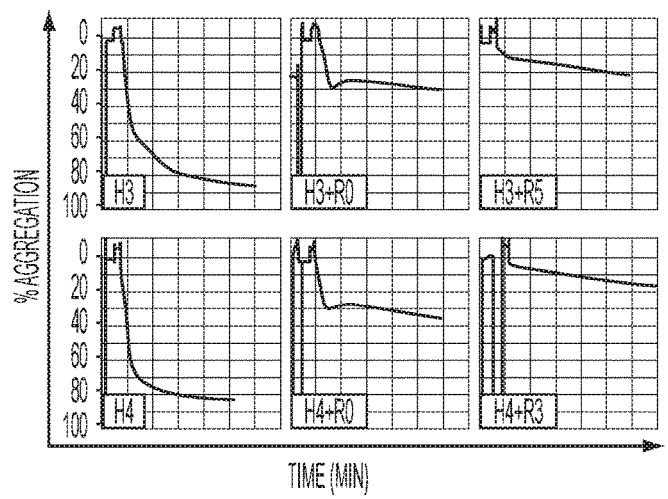
FIGS. 27A-27D. Platelet aggregation data.
Figure 27B:
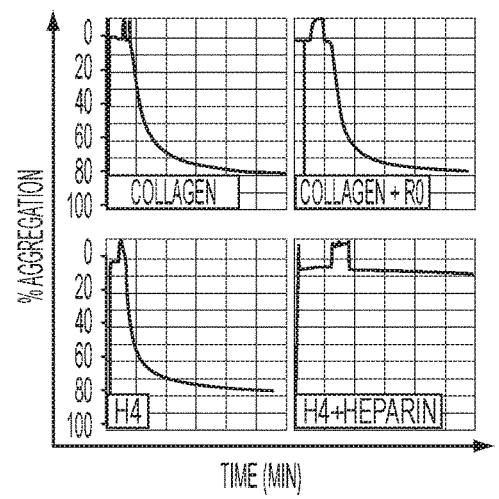
Figure 27C:
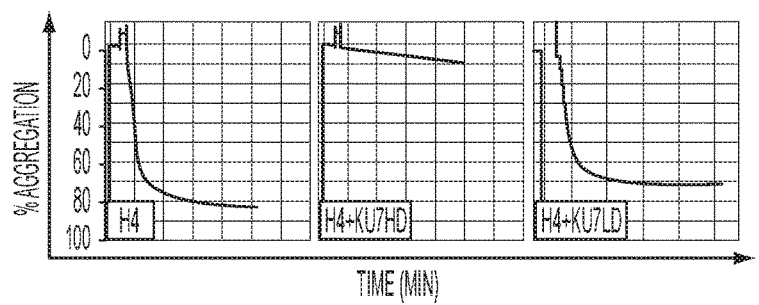
Figure 27D:
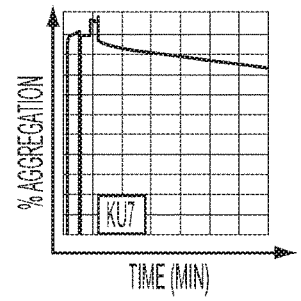

Binding Affinities ($K_D$) of the Different Clones in FIG. 7 for Histones H1, H2A, H2B, H3, and H4 (FIG. 25).

Schematic of Platelet Aggregometer (FIG. 26).

Platelet poor plasma [PPP] is stirred in a cuvette at 37° C. and the cuvette sits between a light course and a photocell. When an agonist is added the platelets aggregate and absorb less light and so the transmission increases and this is detected by the photocell. Schematic adapted from http://practical-haemostasis.com/Platelets/platelet_function_testing_lta.html RNA Aptamers Inhibit Histone-Mediated Platelet Aggregation (FIGS. 27A-27D).

Platelet aggregation was performed with washed human platelets and quantitated using an aggregometer at 2 min intervals. (A) Histones H3 and H4 induce platelet aggregation. Addition of the unselected round 0 aptamer pool (10 nM) reduces platelet aggregation. A more pronounced inhibition of platelet aggregation is observed with selected RNA pools (Rnd5 for H3 and Rnd3 for H4). (B) RNA aptamers have no effect on collagen-mediated platelet aggregation. Heparin (1 U/ml) reverses histone-mediated platelet aggregation. (C) Selected aptamer KU7 high dose (KU7HD, 1000 nM) showed pronounced inhibition of histone H4, while KU7 low dose (100 nM) inhibited only slightly. (D) RNA aptamer KU7 only did not induce platelet aggregation.

Figure 28:
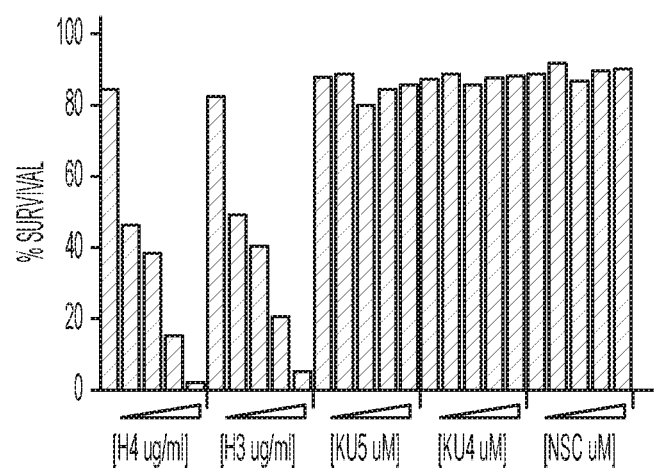
FIG. 28. Cytotoxicity data.

Cytotoxicity of Histones to Endothelial Cells (FIG. 28).

EA.hy926 cells were cultured with human (A) histone H3, (B) histone H4, or (C) aptamers (KU5, KU4, or NSC) for 1 hr at 37° C. Cell damage was measured by flow cytometry for propidium iodide staining. Histone concentration: 0, 12.5, 25, 50, 100 μg/mL and aptamer concentration: 0.0, 12.5, 25, 50, 100 nM. NSC refers to a non-specific control aptamer sequence that does not bind histones.

Figure 29:
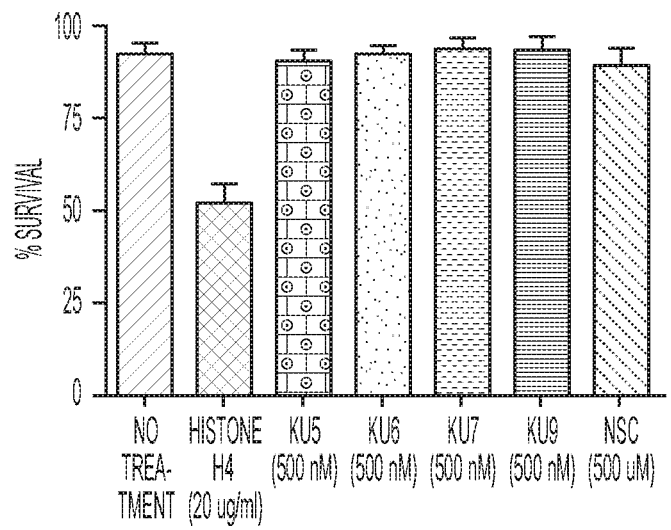
FIG. 29. Cytotoxicity data.

Cytotoxicity Histones to Epithelial Cells (FIG. 29).

Epithelial cells (A549) were incubated With H4 (20 μg/ml) or the aptamers KU5, KU6, KU7, KU9 or control aptamer NSC (all aptamers at 500 uM) concentration for 1 hour. After the hour the cells were treated with propidium iodide and flow cytometry was performed. The percent of all cells that did not stain for P1 are shown.

Figure 30:
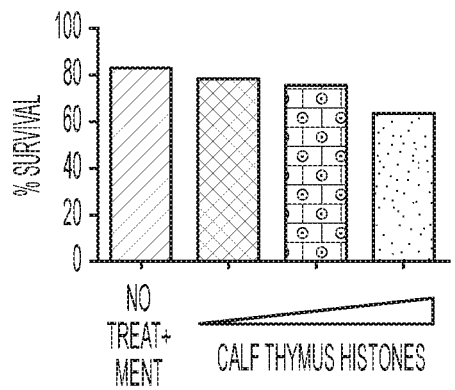
FIG. 30. Cytotoxicity data.

Cytotoxicity of Calf Thymus Histones to Epithelial Cells (FIG. 30).

Epithelial cells (A549) were incubated with calf thymus histones (25, 50, 100 μg/ml) concentration for 1 hour. After the hour the cells were treated with propidium iodide and flow cytometry was performed. The percent of all cells that did not stain for PI are shown.

Figure 31:
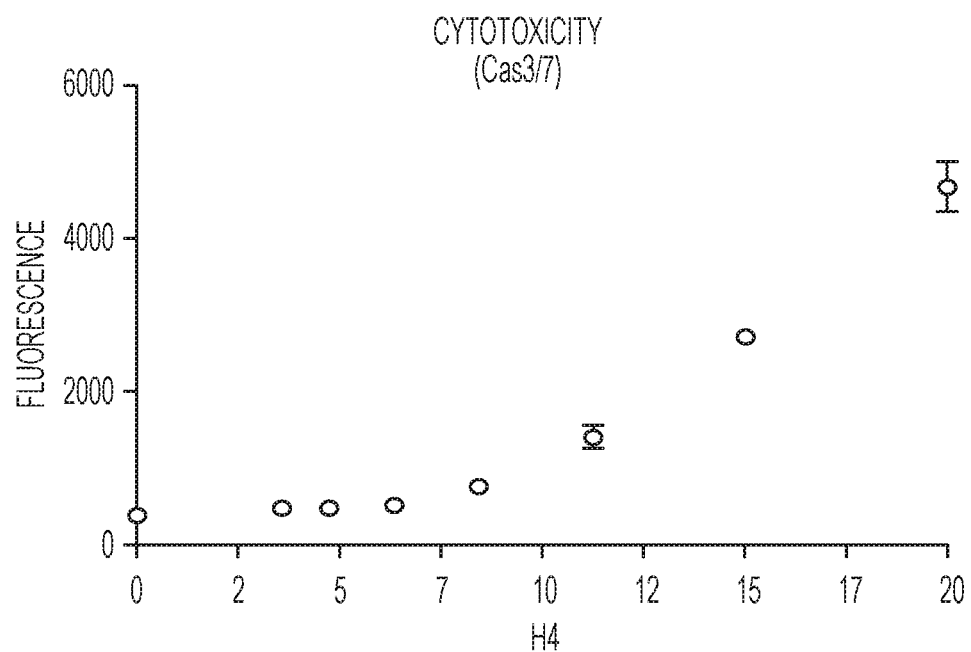
FIG. 31. Cytotoxicity data.

Apoptosis Activation of Histones to Epithelial Cells (FIG. 31).

A549 cells were cultured with human histone H4 for 6 hr at 37° C. Cell apoptosis was measured by florescence using the cellevent Caspase 3/7 kit. Historic concentration: 0, 35.6, 47.5, 63.3, 84.4, 112.5, 150, 200 ug/mL.

Figure 32:
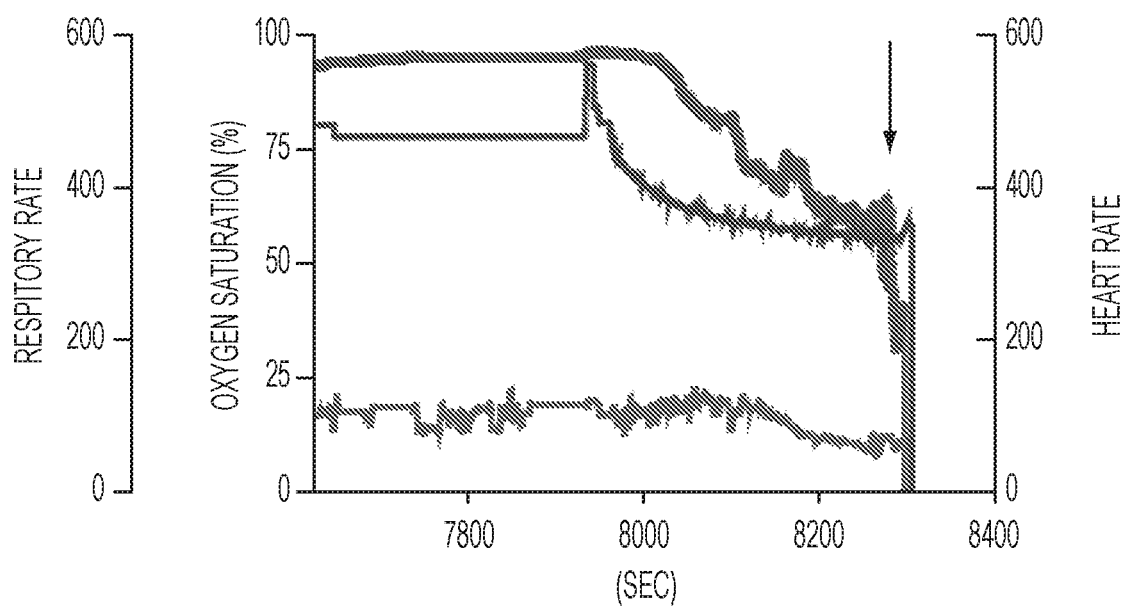
FIG. 32. Mouse data.

Histone Induced Toxicity In Vivo (FIG. 32).

Noninvasive measurement of respiratory rate, heart rate, and oxygen saturation were continuously monitored in a mouse, which was injected with 180 mg/ml of calf thymus histories via tail vein. Arrow indicates time of death. Respiratory rate lowest starting line; % oxygen saturation—highest starting line; heart rate middle starting line.

Summary

As shown in the data above, aptamers were identified that bind to histones H3.2 and H4 using the Systematic Evolution of Ligands by Exponential Enrichment (SELEX) technology (FIG. 5). Following eight rounds of selection (R8), RNA sequences were enriched with overall higher affinity (pM vs. nM range) for the intended histone target compared to the starting, unenriched RNA aptamer library (round 0, R0) (FIG. 12). The progression of the H3.2 and H4 selections was assessed by determining the sequence diversity of the random regions from round to round by high-throughput sequencing (HTS) and identifying enriched sequence and structure families using bioinformatics analysis (FIGS. 7-9). Individual RNA aptamer candidates (9 total) identified from the sequence/bioinformatics analyses were screened to determine binding affinities and specificities (FIGS. 15-24). Binding data are shown for the top nine candidate aptamers (most highly enriched aptamers following 8 rounds of selection) identified from the bioinformatics analysis (FIG. 10). Although the aptamers were selected against H3.2 and H4, binding to histones H1 (FIG. 17-18 and FIG. 23-24), H2A and H2B (FIGS. 23-24) (the equilibrium dissociation constants are reported in the tables) were also determined. The binding data confirm that these aptamers bind with high affinity (KD=pM to low nM range) to histones H3.2 and H4 (FIGS. 23-24). For example, Aptamer KU5 also binds to histones H2A and H2B (affinities in the low nM range) but not H1. Interestingly, aptamer KU7 binds H1 and H2B (KD=low nM range) but not H2A and aptamer KU9 does not bind to histones H2A or H2B but has high affinity for histone H1 (KD=5.3 nM). In addition, binding specificity for the histone proteins was demonstrated by confirming that the RNAs do not bind to proteins in human serum (FIGS. 19-20)

or to human serum albumin (a protein which is highly abundant in serum) (FIGS. 21-22). As an additional measure of specificity, it was confirmed that two control aptamers (NSC and A9g) do not bind to the histone proteins (FIG. 14).

In Vitro Functional Data:

Platelet Aggregation (FIGS. 25-26):

The release of histones from dying cells is associated with microvascular thrombosis. Histone H4 and, to a lesser extent H3.2, have been found to be responsible for directly inducing aggregation of human platelets by driving plasma thrombin generation through the activation of TLR2 and TLR4. It is shown that histones H3.2 and H4 induce pronounced platelet aggregation (plotted as % aggregation), which can be inhibited with addition of heparin (positive control) and the unselected RNA aptamer pool (R0). Importantly, aptamer inhibition of histone-mediated platelet aggregation was more pronounced with selected histone aptamers (data shown for KU7) compared to the unselected RNA pool (R0). As a measure of specificity, the RNA aptamers did not reverse collagen-mediated aggregation.

Aptamer Safety Profile In Vitro (FIGS. 27-31):

Circulating histones cause endothelial cell toxicity, contributing to vascular dysfunction, platelet aggregation and tissue ischemia. It was confirmed that the exposure of cultured epithelial cells with histone H4 (20 ng/ml for 1 hours) results in cell death. In contrast, the candidate histone-selective aptamers (KU5, KU7, KU9) did not induce cell toxicity (1 µM for 1 hour).

Histone-Mediated Toxicity In Vivo (FIG. 32):

Histone administration causes neutrophil migration, endothelial injury and dysfunction, hemorrhage, and thrombosis, which finally result in animal death at doses as low as 50 mg/kg body weight. It was confirmed that injection of histones into the circulation leads to organ failure and subsequent death in a mouse model of multiple organ dysfunction syndrome (MODS). In this experiment, a C57/BL6 mouse was injected with 180 µg/mL of histone from calf thymus while noninvasively monitoring the animal's respiratory rate, heart rate and oxygen saturation. Following intravenous histone injection, oxygen saturation gradually declined over several minutes and the mouse died. These data confirm the acute lung injury caused by circulating histones and identify a model for proposed studies to evaluate the ability of RNA aptamers to protect from histone-mediated lung injury in vivo.

Lengthy table referenced here

US10633410-20200428-T00001

Please refer to the end of the specification for access instructions.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

LENGTHY TABLES

The patent contains a lengthy table section. A copy of the table is available in electronic form from the USPTO web site (http://seqdata.uspto.gov/?pageRequest=docDetail&DocID=US10633410B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10633410B2). An electronic copy of the "Sequence Listing" will also be available from the USPTO upon request and payment of the fee set forth in 37 CFR 1.19(b)(3).

What is claimed is:

1. A method for binding extracellular histone 3 (H3) or histone 4 (H4) in a subject having a histone-induced injury or disease comprising administering to the subject a composition comprising a physiologically acceptable carrier and
   (i) an aptamer having at least 95% identity to KU7 (SEQ ID NO: 7741), wherein the aptamer specifically targets extracellular H3 or H4, wherein the nucleotides are RNA; or
   (ii) a conjugate comprising an aptamer having at least 95% identity to KU7 (SEQ ID NO: 7741), wherein the aptamer specifically targets extracellular H3 or H4, wherein the nucleotides are RNA, wherein the nucleic acid molecule is linked to a therapeutic molecule.

2. The method of claim 1, wherein the administration is by intravenous injection or by inhalation.

3. The method of claim 1, wherein the composition is administered within 0-24 hours after an injury or diagnosis of disease.

4. The method of claim 3, wherein the injury is trauma, burn, transfusion-related acute lung injury, organ ischemia or infarction, or inhalation lung injury.

5. The method of claim 1, wherein the composition is administered more than one time.

6. The method of claim 1, wherein the disease is an autoimmune disease arthritis; edema; sepsis; septic shock; inflammation; infectious disease; thrombosis; traumatic hemorrhage; acute respiratory distress syndrome (ARDS); cardiovascular disease; atherosclerosis; radiotherapy toxicity; cytokine therapy toxicity; granulomatous disease; asthma; graft vs. host disease; cachexia; a coagulopathy; cancer; multiple organ dysfunction syndrome (MODS); or complications thereof.

7. The method of claim 1, further comprising administering at least one therapeutic agent to the subject, before, concurrently with or after the composition.

8. The method of claim 1, wherein the RNA comprises a modified nucleotide.

9. The method of claim 8, wherein the modified RNA comprises a 2' substituted sugar such as 2'-O-methyl-; 2'-O-(2-methoxyethyl); 2-O-alkyl; 2-O-allyl; 2'-S-alkyl; 2'-S-allyl; 2'-fluoro-; 2'-amino; 2'-halo or 2-azido-ribose, a carbocyclic sugar analogue, an a-anomeric sugar; an epimeric sugar such as arabinose, xylose or lyxose, a pyranose sugar, a furanose sugar, sedoheptulose; 2'-fluoro-β-D-arabinonucleotide (FANA) modification; or a Locked nucleic acid (LNA).

10. The method of claim 9, wherein the modified RNA comprises a 2'OMe purine and a 2'-fluoro pyrimidine.

11. The method of claim 1, wherein the therapeutic molecule is an RNAi molecule.

12. The method of claim 1, wherein the aptamer has 100% identity to KU7 (SEQ ID NO: 7741).

13. The method of claim 6, wherein the subject has MODS.

14. A method for binding extracellular histone 3 (H3) or histone 4 (H4) comprising contacting the extracellular H3 or H4 with a composition comprising an aptamer having at least 95% identity to KU7 (SEQ ID NO: 7741), wherein the aptamer specifically targets extracellular H3 or H4, wherein the nucleotides are RNA.

15. The method of claim 14, wherein the RNA comprises a modified nucleotide.

16. The method of claim 15, wherein the modified RNA comprises a 2' substituted sugar such as 2'-O-methyl-; 2'-O-(2-methoxyethyl); 2-O-alkyl; 2-O-allyl; 2'-S-alkyl; 2'-S-allyl; 2'-fluoro-; 2'-amino; 2'-halo or 2-azido-ribose, a carbocyclic sugar analogue, an a-anomeric sugar; an epimeric sugar such as arabinose, xylose or lyxose, a pyranose sugar, a furanose sugar, sedoheptulose; 2'-fluoro-β-D-arabinonucleotide (FANA) modification; or a Locked nucleic acid (LNA).

17. The method of claim 16, wherein the modified RNA comprises a 2'OMe purine and a 2'-fluoro pyrimidine.

\* \* \* \* \*